US009861954B2

(12) United States Patent
Chung et al.

(10) Patent No.: US 9,861,954 B2
(45) Date of Patent: Jan. 9, 2018

(54) POLYOLEFIN INTERPENETRATED NETWORK MATERIAL FOR HYDROCARBON RECOVERY

(71) Applicant: The Penn State Research Foundation, University Park, PA (US)

(72) Inventors: Tze Chiang Chung, University Park, PA (US); Changwoo Nam, University Park, PA (US); Gang Zhang, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 293 days.

(21) Appl. No.: 14/857,440

(22) Filed: Sep. 17, 2015

(65) Prior Publication Data
US 2017/0080404 A1    Mar. 23, 2017

(51) Int. Cl.
*B01J 20/26* (2006.01)
*C07C 7/12* (2006.01)
(Continued)

(52) U.S. Cl.
CPC .......... *B01J 20/267* (2013.01); *B01J 20/261* (2013.01); *B01J 20/264* (2013.01); *B01J 20/3085* (2013.01); *C02F 1/285* (2013.01); *C02F 1/681* (2013.01); *C07C 7/12* (2013.01); *C08F 212/36* (2013.01); *C08J 5/18* (2013.01); *C08J 9/0061* (2013.01); *C08L 23/06* (2013.01); *C08L 23/0815* (2013.01); *C08L 23/18* (2013.01); *C08L 23/20* (2013.01); *C08L 23/24* (2013.01); *C08L 25/08* (2013.01); *C08L 25/16* (2013.01); *C10G 25/003* (2013.01); *E02B 15/00* (2013.01); *C02F 2101/32* (2013.01); *C02F 2103/007* (2013.01); *C02F 2303/16* (2013.01); *C08J 2201/026* (2013.01); *C08J 2205/05* (2013.01);
(Continued)

(58) Field of Classification Search
None
See application file for complete search history.

(56) References Cited

U.S. PATENT DOCUMENTS 4,172,031 A    10/1979  Hall et al.
5,239,007 A    8/1993   Le-Khac
(Continued)

FOREIGN PATENT DOCUMENTS

JP    9-255878 A     9/1997
JP    2004-066054 A  3/2004
WO    2006/036224 A1 4/2006

OTHER PUBLICATIONS

Changwoo Nam et al., "Petrogel: New Hydrocarbon (Oil) Absorbent Based on Polyolefin Polymers," Macromolecules, Jul. 25, 2016, vol. 49, No. 15, pp. 5427-5437.
(Continued)

*Primary Examiner* — Clare M Perrin
(74) *Attorney, Agent, or Firm* — McDermott Will & Emery LLP

(57) ABSTRACT

Interpenetrated polyolefin network for use in recovering or containing hydrocarbons such as hydrocarbons contained in oil, are disclosed. Advantageously, the interpenetrated polyolefin networks absorb the hydrocarbon, including viscous hydrocarbons and crude oils, to form a gel that can be collected and processed by heat to release the collected hydrocarbons.

18 Claims, 5 Drawing Sheets

— Rigid Polyolefin Network (High Tg amorphous polymer)
--- Soft Polyolefin Network (Low Tg amorphous polymer)
● Crosslinker in Both Polyolefin Networks — Rigid Polyolefin Network (Semi-crystalline polymer)
--- Soft Polyolefin Network (Low Tg amorphous polymer)
● Crosslinker in Soft Polyolefin Network

(51) Int. Cl.
*B01D 17/02* (2006.01)
*C02F 1/28* (2006.01)
*B01J 20/30* (2006.01)
*C02F 1/68* (2006.01)
*C08J 5/18* (2006.01)
*C08J 9/00* (2006.01)
*C08L 23/06* (2006.01)
*C08L 23/20* (2006.01)
*C08L 23/24* (2006.01)
*C08L 25/08* (2006.01)
*C08L 25/16* (2006.01)
*C10G 25/00* (2006.01)
*E02B 15/00* (2006.01)
*C08F 212/36* (2006.01)
*C08L 23/08* (2006.01)
*C08L 23/18* (2006.01)
*B01D 15/00* (2006.01)
*C10G 1/04* (2006.01)
*E21B 21/06* (2006.01)
*C09K 8/588* (2006.01)
*C02F 101/32* (2006.01)
*C02F 103/00* (2006.01)

(52) U.S. Cl.
CPC ...... *C08J 2300/208* (2013.01); *C08J 2323/04* (2013.01); *C08J 2323/06* (2013.01); *C08J 2323/20* (2013.01); *C08J 2323/24* (2013.01); *C08J 2325/08* (2013.01); *C08J 2325/16* (2013.01); *C08J 2400/208* (2013.01); *C08J 2423/04* (2013.01); *C08J 2423/06* (2013.01); *C08J 2423/20* (2013.01); *C08J 2423/24* (2013.01); *C08J 2425/08* (2013.01); *C08J 2425/16* (2013.01)

(56) References Cited

U.S. PATENT DOCUMENTS

| | | | |
|---|---|---|---|
| 5,639,541 | A | 6/1997 | Adam |
| 5,641,847 | A | 6/1997 | Hozumi et al. |
| 5,688,843 | A | 11/1997 | Inaoka et al. |
| 6,414,102 | B2 | 7/2002 | Chung et al. |
| 6,485,639 | B1 | 11/2002 | Gannon et al. |
| 6,559,234 | B1 | 5/2003 | Arai et al. |
| 6,881,493 | B2 | 4/2005 | Haveaux et al. |
| 9,109,057 | B2 * | 8/2015 | Chung ............ C02F 1/285 |
| 9,688,895 | B2 * | 6/2017 | Chung ............ C02F 1/285 |
| 2002/0161130 | A1 | 10/2002 | Arai et al. |
| 2012/0046419 | A1 * | 2/2012 | Chung ............ C02F 1/285 |
| 2015/0322186 | A1 * | 11/2015 | Chung ............ C02F 1/285 210/671 |
| 2016/0355715 | A1 * | 12/2016 | Chung ............ C02F 1/285 |

OTHER PUBLICATIONS

International Search Report and Written Opinion issued in Application No. PCT/US2016/048735 dated Dec. 5, 2016.
Zuepei Yuan et al., Novel Solution to Oil Spill Recovery: Using Thermodegradeable Polyolefin Oil Superabsorbent Polymer (Oil-SAP), ASC Publications 2012 American Cancer Society, pp. 4896-4902.
M.O. Adebajo et al., "Porous Materials for Oil Spill Cleanup: A Review of Synthesis and Absorbing Properties", Journal of Porous Materials 10: pp. 159-170, 2003.
Jyongsik Jang et al., "Studies of Crosslinked Styrene—Alkyl Acrylate Copolymers for Oil Absorbency Application. I. Synthesis and Characterization", Journal of Applied Polymer Science, vol. 77, pp. 903-913, 2000.
Ayman M. Atta et al., "Swelling and Network Parameters of High Oil-Absorptive Network Based on 1-Octene and Isodecyl Acrylate Copolymers", Journal of Applied Polymer Science, vol. 97, pp. 80-91 (2005).
Ayman M. Atta et al., "Crosslinked Poly(octadecene-alt-maleic anhydride) Copolymers as Crude Oil Sorbers", Journal of Applied Polymer Science, vol. 105, pp. 2113-2120, (2007).
Guo-Rong Shan et al., "Synthesis and Properties of Oil Absorption Resins Filled with Polybutadiene", Journal of Applied Polymer Science, vol. 89, pp. 3309-3314 (2003).
Deniz Cerylan et al., "Evaluation of Butyl Rubber as Sorbent Material for the Removal of Oil and Polycyclic Aromatic Hydrocarbons from Seawater", Environ. Sci. Technol., 2009, 43, pp. 3846-3852.
Bernard Fouchet, "Diffusion of mineral oil in styrene-butadiene polymer films", Journal of Applied Polymer Science, 111, pp. 2886-2891, 2009.
Mei Hua Zhou et al., "Oil Absorbents Based on Styrene—Butadiene Rubber", Journal of Applied Polymer Science, vol. 89, pp. 1818-1824 (2003).
Mei Hua Zhou et al., "Synthesis and Properties of High Oil-Absorbent 4-tert-Butylstyrene-EPDM-Divinylbenzene Graft Terpolymer", Journal of Applied Polymer Science, vol. 85, pp. 2119-2129 (2002).
Mei Hua Zhou et al., "High oil-absorptive composites based on 4-tert-butylstyrene-EPDM-divinylbenzene graft polymer", Polymer International, 50: pp. 1193-1200 (2001).
Wentian Lin et al., "Cross-Linked Polypropylene Prepared by PP Copolymers Containing Flexible Styrene Groups", Macromolecules 2009, 42, pp. 3750-3754.
L. H. Sperling, "Interpenetrating Polymer Networks and Related Materials", J. Polymer Science: Macromolecular Reviews, vol. 12, pp. 141-180 (1977).
International Search Report and the Written Opinion of the International Searching Authority issued in International Application No. PCT/US2011/048469 dated Apr. 9, 2012.
Hyun-Min Chol et al., "Natural Sorbents in Oil Spill Cleanup", Environ. Sci. Technol. 1992, 26, No. 4, 1992, pp. 772-776.
Ch. Teas et al., "Investigation of the effectiveness of absorbent materials in oil spills clean up", Desalination 140 (2001) pp. 259-264.
Michio Inagaki et al., "Sorption and recovery of heavy oils using carbonized fir firbers and recycling", Carbon 40 (2002) pp. 105-111.
Gerald Deschamps et al., "Oll Removal from Water by Selective Sorption on Hydrophobic cotton Fibers. 1. Study of Sorption Properties and Comparison with Other Cotton Fiber-Based Sorbents", Environ. Sci. Technol., 2003, 37, pp. 1013-1015.
S. Suni et al., "Use of a by-product of peat excavation, cotton grass fibre, as a sorbent for oil spills", Marine Pollution Bulletin 49 (2004) pp. 916-921.
Xiao-Feng Sun et al., "A convenient acetylation of sugarcane bagasse using NBS as a catalyst for the preparation of oil sorption-active materials", Journal of Material Science 38 (2003) pp. 3915-3923.
Reem F. Karag et al., "Synthesis and Characterization of Oil Sorbers Based on Docosanyl Acrylate and Methacrylates Copolymers", Journal of Applied Polymer Science, vol. 109, 2008, pp. 3704-3713.
Guo-Rong Shan et al., "Synthesis and Properties of Oil Absorption Resins Filled with Polybutadiene", Journal of Applied Polymer Science, vol. 89, 3309-3314 (2003).
H.A. Essawy et al., "Oil-Absorptive Polymeric Networks Based on Dispersed Oleophilized Nanolayers of Laponite With Ethylene-Propylene-Diene Monomer Vulanizates", Journal of Applied Polymer Science, vol. 115, 2010, pp. 385-392.
Xiao-Ming Zhou et al., "Synthesis and Characterization of a Novel High-Oil-Absorbing Resin", Journal of Applied Polymer Science, vol. 115, 2010, pp. 3321-3325.
Chitsan Lin et al., "Recycling waste tire powder for the recovery of oil spills", Resources, Conservation and Recycling 52 (2008) pp. 1162-1166.

(56) References Cited

OTHER PUBLICATIONS

V.O.A. Tanobe et al., "Evaluation of Flexible Postconsumed Polyurethane Foams Modified by Polystyrene Grafting as Sorbent Material for Oil Spills", Journal of Applied Polymer Science, vol. 111, pp. 1842-1849, 2009.

Xuepei Yuan et al., "Cross-linking effect on dielectric properties of polypropylene thin films and applications in electric energy storage", Applied Physics Letters 98, 062901-1-062901-3, 2011.

Mei Hua Zhou et al., "Oil Absorbents Based on Styrene-Butadiene Rubber", Journal of Applied Polymer Science, vol. 89, 1818-1824 (2003).

C Praba Karan et al., "Oil Spill Cleanup by Structured Fibre Assembly", Indian Journal of Fibre & Textile Research, vol. 36, Jun. 2011, pp. 190-200.

Tina Arbatan et al., "Superhydrophobic and oleophilic calcium carbonate powder as a selective oil sorbent with potential use in oil spill clean-ups", Chemical Engineering Journal 166 (2011) 787-791.

O.K. Karakasi et al., "Surface modification of high calcium fly ash for its application in oil spill clean up", Fuel 89 (2010) 3966-3970.

Haitao Zhu et al., "Evalation of Electrospur Polyvinyl Chloride/ Polystyrene Fibers as Sorbent Materials for Oil Spill Cleanup", Environ. Sci. Technol. (2011), 45, pp. 4527-4531.

\* cited by examiner

— Rigid Polyolefin Network
(High Tg amorphous polymer)

··· Soft Polyolefin Network
(Low Tg amorphous polymer)

● Crosslinker in Both
Polyolefin Networks

— Rigid Polyolefin Network
(Semi-crystalline polymer)

··· Soft Polyolefin Network
(Low Tg amorphous polymer)

● Crosslinker in Soft
Polyolefin Network

POLYOLEFIN INTERPENETRATED NETWORK MATERIAL FOR HYDROCARBON RECOVERY

STATEMENT REGARDING FEDERALLY SPONSORED RESEARCH

This invention was made with government support under Contract No. E14PC00002 awarded by the U.S. Department of Interior, Bureau of Safety and Environmental Enforcement. The Government has certain rights in the invention.

TECHNICAL FIELD

The present invention relates to polyolefin interpenetrated network material with specific compositions and structures for use in recovering hydrocarbons, such as in absorbing hydrocarbons from crude oil or petroleum products and releasing the recovered hydrocarbons in a separation process.

BACKGROUND

Effective technology for removing, recovering, and cleaning up oil spills or oil slicks from the surface of sea water and shorelines are still needed. Typically, the collection of such spills is carried out by applying materials that absorb and/or adsorb the oil. Adsorption is the adhesion of molecules to the surface of the material and typically results in the oil coating the surfaces (pores and capillaries) of the adsorbent material. Adsorbent materials typically have a microcrystalline matrix that is not readily penetrated by the oil and therefore does not swell when adsorbing oil. On the other hand, absorption is the penetration of molecules to the bulk phase of the material and typically results in the oil contained within the absorbent material. Affinity between the oil and absorbent material drives oil molecules into the absorbent matrix. Highly, absorbent materials with amorphous morphology are usually oil soluble. Cross-linking of such materials is required to maintain the integrity of the absorbent and prevent its dissolution into the oil. Few semi-crystalline polymers with some oil-impenetrable domains can maintain the integrity of the absorbent without cross-linking, but reducing the overall oil absorption capacity.

There have been some studies reporting the sorption (sorption is the general term for adsorption and/or absorption) of spilled oils with inorganic mineral products (i.e. clay, silica, zeolites, etc.) and organic vegetable products (straw, corn cob, peat moss, wood fiber, cotton fiber, etc.) (M. O. Adebajo, R. L. Frost, R. L., J. T. Kloprogge, O. Carmody, S. Kokot, "*Porous materials for oil spill cleanup: a review of synthesis and absorbing properties*", J. Porous Materials, 2003, 10, 159-170). Most of these materials show limited oil absorption capacity and also absorb water; therefore the oil absorbers that are recovered are unsuitable for calcination. Many of these products end-up in land fields after use.

Several synthetic fibers, including highly crystalline polyethylene and polypropylene (PP) fibers (U.S. Pat. No. 5,639,541) and meltblown polypropylene pads and booms (Bayat, et al., *Chem. Eng. Technol.* 2005, 28, 1525) have been disclosed; these materials generally recover oil in their interstices by capillary action. Because the weak oil-substrate interaction, the fiber-based sorbers exhibit many disadvantages, including failure to maintain oil of low viscosity, easy re-bleeding of the sorbed oil under a slight external force, and poor recovery of oil after it has sunk in water.

There are patents disclosing the use of synthetic resins, such as cross-linked styrenic and acrylic copolymers, which absorb oil in their hydrophobic molecular structure. They are all amorphous polymers, cross-linking is needed to prevent the polymer from dissolving in the oils (U.S. Pat. Nos. 5,239,007; 5,641,847; and 5,688,843). Such material have the advantage of selectively absorbing oil floating on the surface of water, and have good oil-maintaining properties of absorbed oil. However, these synthetic resins have the drawback of a long absorbing time in comparison with that of fibers. In particular, they fail to absorb high viscosity oil within a short time. Some methods, i.e. milling the oil absorber to increase surface area, were proposed to improve the oil absorbing speed for high viscosity oil, but were met with limited success. The milled oil absorbers are liable to aggregate, thereby the gel block phenomenon prevents the admission of oil to be absorbed into further gaps between the particles of oil absorber.

Further, there are literature reports disclosing the use of cross-linked amorphous styrene/acrylate (Jang, et al., *J. Appl. Polym. Sci.* 2000, 77, 903), 1-octene/acylate (Atta, et al., *J. Appl. Polym. Sci.* 2005, 97, 80), and octadecene/maleic anhydride copolymers (Atta, et al., *J. Appl. Polym. Sci.* 2007, 105, 2113). However, these resins contain some hydrophilic polar groups and require additional procedures for cross-linking reaction after copolymerization, and having the drawback of a long absorbing time, especially for aliphatic hydrocarbon components. Some synthesized rubbers, with amorphous morphology and low Tg (glass transition temperature), such as polybutadiene (Shan, et al., *J. Appl. Polym. Sci.* 2003, 89, 3309), butyl rubber (Ceylan, et al., *Environ Sci. Technol.* 2009, 43, 3846), SBR (Fouchet, B., *J. Appl. Polym. Sci.* 2009, 111, 2886), and EPDM (Zhou, et al., *J. Appl. Polym. Sci.* 2003, 89, 1818), were also modified (grafting and cross-linking) to achieve the network structure for oil absorption. However, the solution cross-linking procedure typically used with such materials is not controlled. Moreover, these materials usually require extensive solvent extraction to remove any soluble polymer fraction prior to use (Zhou, et al., *J. Appl. Polym. Sci.* 2002, 85, 2119 and *Polym International* 2001, 50, 1193), and the resulting sol-free materials possess various degree of cross-linking density that reduces the overall oil swelling capability. Furthermore, most of the oil absorption tests were conducted using refined oil products (such as mineral oil), organic solvents (such as toluene), or diluted crude oil (10 weight % in toluene). Some methods, i.e. milling, electric-spinning, and foaming of the oil absorbents to increase surface area, were applied to improve the oil absorbing speed. So far, there does not appear to be reports showing a high oil absorbent capacity for natural crude oils.

A new class of cross-linked polyolefin terpolymers for use in recovering hydrocarbons was recently reported. See Chung, et al. *Energy Fuels* 2012, 26, 4896; U.S. Patent Publication No. 2012-0046419 and U.S. Pat. No. 9,109,057. This new class of cross-linked polyolefin terpolymers provide many benefits, including (a) high oil absorption capacity, (b) fast sorption kinetics, (c) little to no water absorption, (d) buoyancy for easy recovery from the surface of water and good mechanical strength, (e) the recovered oil-polymer composition is suitable for use in a typical commercial oil refining processes, and (f) cost effectiveness. However, such cross-linked polyolefin terpolymers are less efficient for absorbing high molecular weight hydrocarbons with high viscosity and complex crude oils such as those that contain a whole spectrum of hydrocarbons up to >$C_{30}$. In addition, such cross-linked polyolefin terpolymers do not readily form films or foams.

Accordingly, there is a continuing need for absorbent materials that can quickly collect and retain high molecular weight hydrocarbons, crude oils, and other such hydrocarbons, as is necessary in the case of oil spills and oil contaminated areas and liquids. Furthermore, there is also a need for absorbent materials that can be readily prepared as films and foams and advantageously minimize the treatment of the absorbent after use, including waste disposal, and improve recyclability and biodegradability of the recovered absorbent.

SUMMARY OF THE DISCLOSURE

Advantages of the present disclosure include polymers, compositions, structure, and methods for containment, collection, separation and/or recovering of hydrocarbons, such as a mixture of hydrocarbons contained in crude oil, from an environment, such as surface water, shorelines, or an enclosed environment such as a container or vessel.

Additional Advantages of the present disclosure include the hydrocarbon super-absorbent exhibits a combination of benefits in the hydrocarbon recovery and cleanup, including (i) high oil absorption capability, (ii) fast kinetics, (iii) easy recovery from water surface, (iv) no water absorption, (v) the recovered oil-swelled hydrocarbon gel as regular crude oil for refinery, (vi) no waste in natural resources and no air/water pollutions, and (vii) cost effective and economic feasible.

These and other advantages are satisfied, at least in part, by a polyolefin interpenetrated network comprising a soft polyolefin network and a rigid polyolefin network. The rigid polyolefin network advantageously is either an amorphous polyolefin network with a Tg of at least 50° C. or a semi-crystalline polyolefin with a Tm of no less than 35° C. The soft polyolefin network can be represented by formula (I)

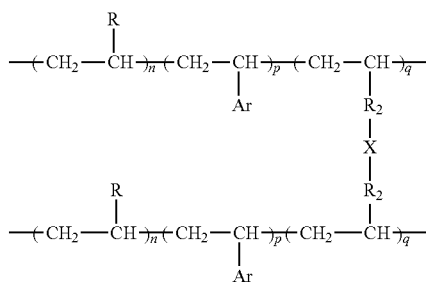

wherein ($CH_2$—CH(R)) represents the same or different olefin repeating unit; R is independently H or a $C_1$-$C_{28}$ linear, branched, or cyclic alkyl moiety; n is an integer greater than about 500; ($CH_2$—CH(Ar)) represents the same or different aromatic repeating unit; Ar is an aryl moiety that can be substituted with one or more $R_1$ groups; wherein $R_1$ is a $C_1$ to $C_{10}$ linear, branched, or cyclic alkyl moiety that can be substituted with one or more $C_1$ to $C_5$ alkyl groups; p is an integer in the range from 0 to 15,000; $R_2$ is either present or absent and when $R_2$ is present, $R_2$ is a $C_1$ to $C_{10}$ linear, branched, or cyclic alkyl moiety that can be substituted with one or more $C_1$ to $C_5$ alkyl groups; X is a cross-linking moiety resulting; and q is an integer greater than about 5.

In some embodiments, the rigid polyolefin network is represented by formula (II):

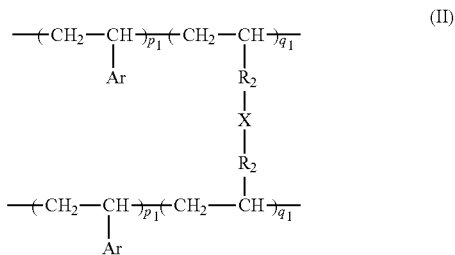

wherein ($CH_2$—CH(Ar)) represents the same or different aromatic repeating unit; Ar is an aryl moiety that can be substituted with one or more $R_1$ groups; wherein $R_1$ is a $C_1$ to $C_{10}$ linear, branched, or cyclic alkyl moiety that can be substituted with one or more $C_1$ to $C_5$ alkyl groups; p1 is an integer greater than about 500; $R_2$ is either present or absent and when $R_2$ is present, $R_2$ is a $C_1$ to $C_{10}$ linear, branched, or cyclic alkyl moiety that can be substituted with one or more $C_1$ to $C_5$ alkyl groups; X is a cross-linking moiety; and q1 is an integer greater than about 5.

In other embodiments, the rigid polyolefin network is represented by formula III:

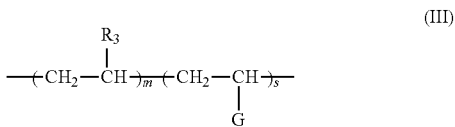

wherein ($CH_2$—CH($R_3$)) represents a $C_2$-$C_8$ alpha olefin; $R_3$ is independently H or a $C_1$-$C_6$ linear, branched, or cyclic alkyl or aromatic moiety; m is an integer greater than about 500, G is a pendant side group, which is different from $R_3$ and can be linear or branched alkyl group, or a cyclic aliphatic or aromatic group; s is an integer in the range from 0 to 5,000; and the ratio of m to s is greater than about 5.

In till further embodiments, the rigid polyolefin network is a semi-crystalline polyolefin thermoplastic that has a Tm of not less than about 35° C.

Another aspect of the present disclosure includes a process of making a polyolefin interpenetrated network by mixing a precursor to the soft polyolefin network of formula (I) with a precursor to the rigid polyolefin network and then forming the network structures of the polyolefins.

Another aspect of the present disclosure includes a method of recovering hydrocarbon by contacting at least one hydrocarbon with the polyolefin interpenetrated network to absorb the at least hydrocarbon in the polyolefin interpenetrated network.

In an aspect of the present disclosure, a method of recovering hydrocarbon includes heating an interpenetrated polyolefin network comprising a soft polyolefin network and a rigid polyolefin network and containing at least one liquid hydrocarbon to release the at least liquid hydrocarbon from the interpenetrated polyolefin network.

An additional advantage of the present invention is a method of recovering a hydrocarbon by contacting at least one hydrocarbon or a mixture of hydrocarbons, such as contained in petroleum or crude oil, with a polyolefin interpenetrated network to absorb the hydrocarbon into the polyolefin interpenetrated network.

Advantageously, the polyolefin interpenetrated network can be prepared into various product forms, such as films, sheets, fibers, pipes, rods, pellets, powders, and open porous foams with high surface areas. Preferably, the polyolefin interpenetrated network has a short absorbate diffusion path to absorb the hydrocarbon (including viscous hydrocarbons and crude oils) with fast kinetics and high capacity to form a gel (i.e., a hydrocarbon-polyolefin composition). The hydrocarbon-polyolefin composition can be formed without containing water even in an aqueous environment and can float on the surface of water. The polyolefin interpenetrated network of the present disclosure can also advantageously be a self-supporting network and retain mechanical integrity even after absorbing hydrocarbons with more than 40 times of its original weight. Furthermore, the polyolefin interpenetrated network of the present disclosure can also advantageously be collected and processed by heat to release the collected hydrocarbon and substantially decompose the polyolefin interpenetrated network, preferably into low molecular weight hydrocarbons. The release of hydrocarbon and decomposition of the polyolefin interpenetrated network can advantageously be carried out in a typical commercial oil refining process such that the hydrocarbon-polyolefin composition can be treated in more or less the same manner as an oil feedstock in a refining process.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

Figure 1A:
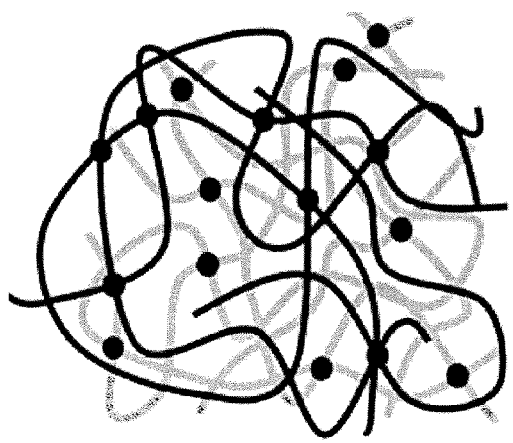
FIGS. 1A and 1B are schematic representations of polyolefin interpenetrated network materials that contain a soft (low Tg) crosslinked amorphous polyolefin network and a rigid polyolefin network, either a high Tg crosslinked amorphous polyolefin network (A) or a semicrystalline polyolefin network (B), according to an embodiment of the present disclosure.

The present disclosure relates to new absorbent polymers, i.e. an absorbent polyolefin interpenetrated network that can advantageously absorb one or more hydrocarbons, such as hydrocarbons contained in crude oil, petroleum products, waste water, or areas containing one or more hydrocarbons.

The polyolefin interpenetrated network of the present disclosure is comprised of two independent polyolefin networks, i.e., a soft polyolefin network and a rigid polyolefin network. The combination of a soft polyolefin network with a rigid polyolefin network provides the polyolefin interpenetrated network with several advantages over its individual components. While the soft polyolefin network provides high absorption capacity, it tends to have poor handling and mechanical properties. Optimizing the absorption capacity of the soft polyolefin network, typically requires reducing the crosslink density of the polymer which in turn typically makes the polymer sticky and lowers the mechanical strength and consequently lowers the handling properties of the soft polyolefin network polymer. Further once crosslinked, the soft polyolefin network is not readily amenable to be processed into films or porous forms. Thus, there is a trade-off in terms of optimizing the absorption capacity and the mechanical properties for the soft polyolefin network.

It was discovered that by combining the soft polyolefin network with a rigid polyolefin network, the handling properties of the soft polyolefin network could be significantly improved without significantly adversely affecting the hydrocarbon capacity of the soft polyolefin network. In fact, it was surprisingly discovered that the combination of soft polyolefin network with a rigid polyolefin network has a hydrocarbon absorption capacity that was greater than either component alone, and even greater than simply adding the capacity of the individual components. It was further discovered that by combining the soft polyolefin network with a rigid polyolefin network allowed for sufficient mechanical strength to readily form films, foams, powders, etc. of the polyolefin interpenetrated network.

The polyolefin interpenetrated network of the present disclosure can absorb several fold, e.g., 2 to 10 times, more hydrocarbon than either the soft polyolefin network or the rigid polyolefin network alone. After contacting the polyolefin interpenetrated network of the present disclosure with hydrocarbon to forma a hydrocarbon-polyolefin composition, the resulting composition can contain little to no water even in an aqueous medium and can float on the surface of water with self-supporting network structure that can be mechanically recovered, without leaking oil. Furthermore, the polyolefin interpenetrated network can be decomposed back to low molecular weight hydrocarbons (e.g., hydrocarbons that are liquid at below about 100° C.) such that the decomposition of the polyolefin interpenetrated network does not result in a carbon residue upon heat treatment and can be treated in more or less the same manner as an oil feedstock in a refining process. The combined properties of the polyolefin interpenetrated network of the present disclosure can thus offer a new comprehensive approach in dealing with recovering hydrocarbons (including crude oil) with minimum environmental impact and the loss of natural resource.

In one aspect of the present disclosure, the polyolefin interpenetrated network is composed of a soft polyolefin network that is chemically crosslinked and has a low glass transition temperature (Tg) and a rigid polyolefin network that has its network structure due to chemical crosslinks or due to physical crosslinks such as crystalline domains.

Each polyolefin network is preferably formed by one or more olefinic monomers with a high affinity for a target hydrocarbon, or mixture of hydrocarbons for absorption. The polyolefin networks of the present disclosure have either crosslinking units or crystalline domains so that the polyolefin does not dissolve in the target hydrocarbon at ambient temperatures, i.e., at or below a temperature of 25° C. Preferably, the polyolefins of the present disclosure contain both aliphatic and aromatic repeating units, as well as either the crosslinking units or some crystalline domains. For increased absorption rates, the crosslinked polyolefins have a complete, but lightly cross-linked network structure, and the semi-crystalline polyolefins have relatively low melting temperature (but not less than about 35° C.) and low degree of crystallinity (preferably not less than about 10% degree of crystallinity).

For example, the soft polyolefin network can have the following independent features, including an amorphous morphology; a low Tg (as determined by differential scanning calorimetry (DSC) described herein or equivalent equipment and procedures), e.g., a Tg of no more than about 10° C., such as less than about 0° C. or −10° C.; and a large free volume.

The rigid polyolefin network can be either (i) a cross-linked, amorphous polyolefin with a high Tg (as determined by DSC described herein or equivalent equipment and procedures), e.g., a Tg of at least about 50° C., such as at or above about 60° C. or 80° C., or (ii) a semi-crystalline polyolefin thermoplastic with the following independent features, including the semi-crystalline morphology, a Tm at or above about 35° C. (as determined by DSC described herein or equivalent equipment and procedures), e.g., a Tm of above about 35° C. and less than about 80° C., such as between about 35° C. and about 55° C.; and a low degree of crystallinity with the fraction of the ordered polymer chains below about 30% and as low as about 10%.

In an embodiment of the present disclosure, the polyolefin interpenetrated network has a weight ratio of from about 1:10 to about 10:1 of the soft polyolefin network to the rigid polyolefin network, e.g., from about 1:5 to about 5:1, such as from about 1:3 to about 3:1 of the soft polyolefin network to the rigid polyolefin network. The soft polyolefin network and rigid polyolefin network are preferably intertwined in the polyolefin interpenetrated network at least to such a degree that contacting the polyolefin interpenetrated network with hydrocarbons does not result in a significant dissolution or separation of the soft polyolefin network and/or rigid polyolefin network despite a high affinity for absorbing the hydrocarbon in to the polyolefin interpenetrated network. In an embodiment of the present disclosure, the polyolefin interpenetrated network is in the form of either an interpenetrating polymer network (IPN) or a semi-interpenetrating polymer network (SIPN) but the polyolefin interpenetrated network is not limited to either an IPN or SIPN.

As is known in the field, an IPN is a polymer comprising two or more polymer networks which are at least partially interlaced on a molecular scale but not covalently bonded to each other and cannot be separated unless chemical bonds are broken. See. L. H. Sperling, "*Interpenetrating polymer networks and related materials*", J. Polymer Sci.: Macromolecular Reviews, 1977, 12, 141-180. The two or more networks can be envisioned to be entangled in such a way that they are concatenated and cannot be pulled apart, but not bonded to each other by any chemical bond. Simply mixing two or more polymers does not create an interpenetrating polymer network (polymer blend), nor does creating a polymer network out of more than one monomers to form one network (copolymer). Most of IPN polymers were prepared by two-step sequential polymerization process. After forming first crosslinked polymer network, this polymer network is swollen with second monomer, plus crosslinker and initiator, and polymerized in situ to form second crosslinked polymer network that is interlaced with the first polymer network. By nature of network structure, the IPN materials as prepared are thermosets and cannot be processed and reformed. Many research efforts were devoted in fine-tuning synthesis sequences and crosslinking density, in conjunction with emulsion and suspension processes in some cases, to improve their molding and film-casting capability with limited success.

An SIPN is a polymer comprising one or more networks and one or more linear or branched polymer(s) characterized by the penetration on a molecular scale of at least one of the networks by at least some of the linear or branched macromolecules.

The combination of network structure and molecular-level mixing morphology offers IPN and SIPN materials with unique synergistic properties that both individual networks do not have. If one polymer is plastic and the other elastic in the application temperature, the IPN material performs either impact-resistant plastics or reinforced rubber depending on which phase predominates. In the polyolefin interpenetrated network of the present disclosure, the soft polyolefin network with strong affinity to hydrocarbons provides maximum absorption capacity and the rigid polyolefin network with better mechanical strength provides the desirable morphology to enhance absorption kinetics and recovery.

Figure 1B:
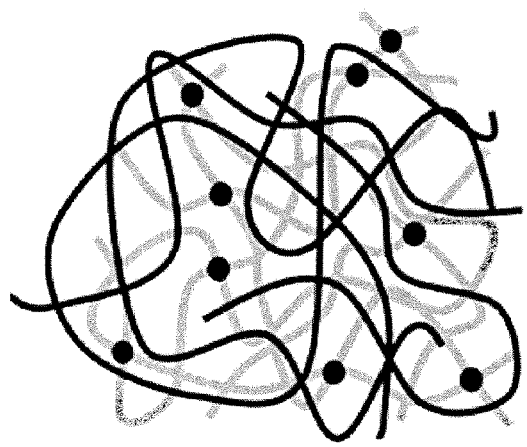

As a schematic representation of an embodiment of the present disclosure, FIGS. 1A and 1B present two types of polyolefin interpenetrated network materials, in which a rigid polyolefin network and a soft polyolefin network are interpenetrated and both polymers are uniformly distributed in the whole network structure. The soft polyolefin network is an amorphous polyolefin copolymer with a low Tg of less than about 10° C. and high free volume (due to side chains and/or pendant groups from monomer units) and a network structure (due to the cross-linking in its matrix). The rigid polyolefin is either a cross-linked amorphous polyolefin (shown in Scheme A) with a high Tg of more than about 50° C. and a network structure (due to the cross-linking in its matrix) or a semi-crystalline polyolefin thermoplastic (shown in Scheme B) and a network structure (due to some insoluble crystalline domains in its matrix).

The polyolefin interpenetrated network of the present disclosure is preferably completely insoluble in hydrocarbons under ambient conditions, i.e., at temperatures at or below 25° C. Advantageously, the polyolefin interpenetrated network can have durable self-supporting mechanical properties and can be processed into film and foam structures with high surface area such that it reduces absorbate (hydrocarbon) diffusion path into the matrix. During absorbing hydrocarbons, the matrix swells its volume to form a hydrocarbon-polyolefin composition (i.e., gel). The combination of high affinity between the hydrocarbon and/or polymer and/or side chains or pendant groups off of the backbone of polyolefin and the open morphology with high surface area for shortening absorbate diffusion path enhances the hydrocarbon absorption capacity and kinetics, especially in the cases of absorbing viscous hydrocarbons and crude oils with high molecular weights and complex mixtures.

In practicing an embodiment of the present disclosure, at least one hydrocarbon, or preferably a mixture of hydrocarbons, such as in crude oil or a petroleum product, is recovered by contacting the at least one hydrocarbon with a polyolefin interpenetrated network. Hydrocarbons of particular interest include, one or more of, or a mixture of aliphatic and aromatic hydrocarbons (e.g., alkanes, such as pentane, hexane, cyclohexane, heptane, octane; alkenes, such as pentene, hexene, heptene, octene; aromatics such as benzene, toluene, xylene), common petroleum products (e.g., paraffins, naphtha, gasoline, kerosene, diesel, fuel oil, etc.), hydrocarbons contained in waste water, such as formed through oil recovery process, etc. By this process, the polyolefin interpenetrated network absorbs the at least one hydrocarbon to form a gel. Advantageously, the gel comprises the polyolefin and the hydrocarbon. The polyolefin interpenetrated network with specific composition and morphology can be optimized for recovering a particular hydrocarbon or mixture of hydrocarbons by selecting appropriate olefinic monomers and crosslinking monomers to prepare the soft polyolefin network and by selecting appropriate olefinic monomers and optionally crosslinking monomers to prepare the rigid polyolefin network.

In one aspect of the present disclosure, the hydrocarbon absorption capacity of a polyolefin interpenetrated network is greater than about 10. The absorption capacity as used herein is determined according to the measurement method described further below. In other embodiments of the present disclosure, the polyolefin interpenetrated network material has an absorption capacity that is greater than about 20, about 30 and even greater than about 40.

In one aspect of the present disclosure, the polyolefin interpenetrated network is formed from several aliphatic and aromatic olefinic monomers and crosslinkers. The aliphatic olefinic monomer includes one or more aliphatic olefins selected from ethylene, propylene, 1-butene, 1-pentene, 1-hexene, 1-heptene, 1-octene, 1-nonene, 1-decene, 3-methyl-1-butene, 4-methyl-1-pentene, 3-methyl-1-pentene, 4-methyl-1-hexene, 3,3-dimethyl-1-butene, and 4,4-dimethyl-1-hexene, and combinations thereof. The aromatic olefinic monomer includes one or more aromatic olefins selected from styrene, alkylstyrenes, such as p-methylstyrene, o-methylstyrene, m-methylstyrene, 2,4-dimethylstyrene, 2,5-dimethylstyrene, 3,4-dimethylstyrene, 3,5-dimethylstyrene and t-butylstyrene, and a combination thereof. Furthermore, the cross-linker can be selected from non-conjugated diene, including 1,5-hexadiene, 1,7-octadiene, 1,2-divinylbenzene, 1,3-divinylbenzene, 1,4-divinylbenzene, 4-propenylstyrene, 4-butenylstyrene, 4-pentenylstyrene, 4-hexenylstyrene, and a combination thereof.

The soft polyolefin network in the polyolefin interpenetrated network can be formed from about 70-99.9 mole % of one or more aliphatic olefins, e.g., a $C_{4-12}$ alpha olefin such as 1-octene, 1-decene; from about 0 to 30 mole % of one or more aromatic monomer, e.g., a styrene; and from about 0.1 to 3 mole %, e.g., 0.1 to about 2% of a cross-linker, e.g. divinylbenzene. The rigid polyolefin network can be formed from one or more aromatic olefins, e.g. a styrene; and from about 0.1 to 3 mole %, e.g., 0.1 to about 2% of a cross-linker, e.g. divinylbenzene. Furthermore, the rigid polyolefin network can also be formed from a semi-crystalline polyolefin thermoplastic that has a Tm of not less than about 35° C., such as semicrystalline polyethylene including low density polyethylene (LDPE), linear low density polyethylene (LLDPE), high density polyethylene (HDPE), isotactic polypropylene (i-PP), and syndiotactic polystyrene (s-PS) homo- and co-polymers. Such semicrystalline polymers are not soluble in hydrocarbons under ambient conditions. The preferred polyolefin thermoplastics have a semicrystalline morphology with a low melting temperature, e.g., a Tm of between about 35° C. and about 80° C.; and a low degree of crystallinity with the fraction of the ordered polymer chains below about 30% and as low as about 10%.

Alternatively and separately, the soft polyolefin network in the polyolefin interpenetrated network material of the present disclosure can be represented by the following formula (I):

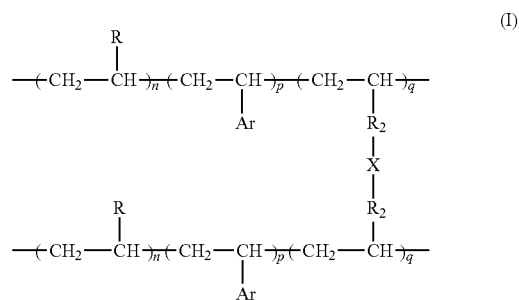

wherein ($CH_2$—$CH(R)$) represents the same or different olefin repeating unit, e.g. a $C_2$-$C_{30}$ alpha olefin; R is independently H or a $C_1$-$C_{28}$ linear, branched, or cyclic alkyl moiety; n is an integer greater than about 500, e.g., between about 500 and 50,000; ($CH_2$—$CH(Ar)$) represents the same or different aromatic repeating unit, e.g., a styrene unit; Ar is an aryl moiety that can be substituted with one or more $R_1$ groups; wherein $R_1$ is a $C_1$ to $C_{10}$ linear, branched, or cyclic alkyl moiety that can be substituted with one or more $C_1$ to $C_5$ alkyl groups; p is an integer in the range from 0 to 15,000, e.g., 50 to 15,000. Since "p" can be zero it is understood that the crosslinked polyolefin does not necessarily contain ($CH_2$—$CH(Ar)$) units. The variable $R_2$ is either present or absent. When $R_2$ is present, $R_2$ is a $C_1$ to $C_{10}$ linear, branched, or cyclic alkyl moiety that can be substituted with one or more $C_1$ to $C_5$ alkyl groups; X is a cross-linking moiety resulting from a thermal induced cycloaddition reaction between two pendent olefinic units; and q is an integer greater than about 5, e.g., from about 5 to about 100. Preferably the soft polyolefin network of formula (I) has an amorphous morphology and/or a low Tg, e.g., a Tg of no more than about 10° C., such as less than about 0° C. or −10° C.

In one embodiment of the present disclosure, ($CH_2$—$CH(R)$) represents the same or different $C_2$-$C_{30}$ alpha olefin, e.g., the same or different $C_4$-$C_{12}$ alpha olefin such as ethylene, propylene, 1-butene, 1-pentene, 1-hexene, 1-heptene, 1-octene, 1-nonene, 1-decene, 3-methyl-1-butene, 4-methyl-1-pentene, 3-methyl-1-pentene, 4-methyl-1-hexene, 3,3-dimethyl-1-butene, and 4,4-dimethyl-1-hexene, and combinations thereof; ($CH_2$—$CH(Ar)$ represents the same or different styrene monomer and the pendant aromatic moiety (Ar) selected from the group consisting of phenyl, p-methylphenyl, o-methylphenyl, m-methylphenyl, 2,4-dimethylphenyl, 2,5-dimethylphenyl, 3,4-dimethylphenyl, 3,5-dimethylphenyl and p-t-butylphenyl, and combinations thereof; p can be zero; ($CH_2$—CH)—$R_2$—X—$R_2$—(CH—$CH_2$) is formed by the cycloaddition of two pendent styrene units, e.g. between two divinylbenzene units; and p is 0 or the ratio of n to p is greater than about 2, e.g., greater than about 3 or 4.

Alternatively and separately, the rigid polyolefin network in the polyolefin interpenetrated network of the present disclosure can be represented by the following formula (II):

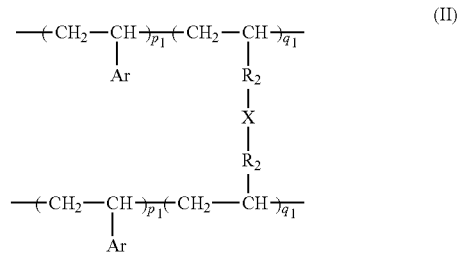

wherein (CH$_2$—CH(Ar)) represents the same or different aromatic repeating unit, e.g., a styrene unit; Ar is an aryl moiety that can be substituted with one or more R$_1$ groups; wherein R$_1$ is a C$_1$ to C$_{10}$ linear, branched, or cyclic alkyl moiety that can be substituted with one or more C$_1$ to C$_5$ alkyl groups; p1 is an integer greater than about 500, e.g., between about 500 and 50,000. The variable R$_2$ is either present or absent. When R$_2$ is present, R$_2$ is a C$_1$ to C$_{10}$ linear, branched, or cyclic alkyl moiety that can be substituted with one or more C$_1$ to C$_5$ alkyl groups; X is a cross-linking moiety resulting from a thermal induced cycloaddition reaction between two pendent olefinic units; and q1 is an integer greater than about 5, e.g., from about 5 to about 100. Preferably the rigid polyolefin network of formula (II) has a high Tg, e.g., a Tg of at least about 50° C., such as at or above about 60° C. or 80° C.

Further, both cross-linked polyolefins of formula (I) and (II) of the present disclosure can also be formed by thermal reactions between two or more pendant pendent thermally crosslinkable olefinic units on the polyolefin chain. Such pendant pendent thermally crosslinkable olefinic units include residues from one or more repeating units selected from a non-conjugated diene, including 1,5-hexadiene, 1,7-octadiene, 1,2-divinylbenzene, 1,3-divinylbenzene, 1,4-divinylbenzene, 4-propenylstyrene, 4-butenylstyrene, 4-pentenylstyrene, 4-hexenylstyrene, and a combination thereof. The vinyl residues can be either linked directly to the chain or with an alkyl or aryl spacer. For example, in the formula above, X can be a cross-linking moiety that is a residue formed by a thermal cycloaddition reaction between two pendant styrene units. Alternatively and separately, X can be a cross-linking moiety that is a residue formed by an addition reaction between pendant olefin units or between a styrene unit and a pendent olefin unit. Furthermore, the cross-linking reaction can occur between the two networks of formula (I) and (II) as well as within the individual network of formula (I) and (II).

In another alternative and separate aspect of the disclosure, the rigid polyolefin network in the polyolefin interpenetrated network of the present disclosure can be a semi-crystalline polyolefin thermoplastic, which can be represented by the following formula (III):

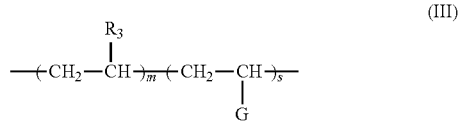

wherein (CH$_2$—CH(R$_3$)) represents a C$_2$-C$_8$ alpha olefin; R$_3$ is independently H or a C$_1$-C$_6$ linear, branched, or cyclic alkyl or aromatic moiety; m is an integer greater than about 500, e.g., between about 500 and 50,000. The preferred alpha olefin is ethylene, propylene, 1-butene, 1-pentene, 1-hexene, 4-methyl-1-pentene, and styrene. G is a pendant side group, which is different from R$_3$ and can be linear or branched alkyl group, or a cyclic aliphatic or aromatic group. Preferably, G is a C$_1$ to C$_{10}$ linear or branched alkyl group or a C$_6$ to C$_{10}$ substituted or unsubstituted aromatic group, and most preferably, G is C$_1$ to C$_6$ alkyl group or substituted or unsubstituted C$_6$ aromatic group; s is an integer in the range from 0 to 5,000; and the ratio of m to s is greater than about 5, e.g., greater than about 10 or 15. It is preferable that when R$_3$ a C$_1$-C$_4$, i.e., (CH$_2$—CH(R$_3$)) is not an ethylene unit, the R$_3$ groups in the incorporated (CH$_2$—CH(R$_3$)) units are arranged predominately in either isotactic or syndiotactic steric arrangement along the polymer chains so that the rigid polyolefin of formula (III) is semi-crystalline. Preferably, the rigid polyolefin network of formula (III) is a semi-crystalline polyolefin thermoplastic that has a Tm of not less than about 35° C. and has no chemical crosslinks.

In one embodiment of the present disclosure, formula (III) represents a semi-crystalline polyolefin thermoplastic, including low density polyethylene (LDPE), linear low density polyethylene (LLDPE), high density polyethylene (HDPE), isotactic polypropylene (i-PP), and syndiotactic polystyrene (s-PS) polymers. Such semi-crystalline polyolefin thermoplastic are not soluble in any hydrocarbon under ambient conditions. The preferred polyolefin thermoplastics have a semi-crystalline morphology with a melting temperature (Tm) of not less than 35° C. and in some embodiments a Tm of between about 35° C. and about 80° C., such as between about 35° C. and 55° C.; and a low degree of crystallinity with the fraction of the ordered polymer chains below about 30% and as low as about 10%. Such semi-crystalline polyolefin thermoplastics have no chemical crosslinks but are rigid polyolefin network polymers because of the crystalline domains.

In one aspect of the present disclosure, each individual polyolefin in formula (I), (II), and (III) is prepared by transition metal coordination polymerization mechanism using some selective heterogeneous Ziegler-Natta and homogeneous (single-site) metallocene catalysts. The resulting linear polymers (before thermal crosslinking reaction) are soluble in organic solvents with a relatively high molecular weight, e.g., M$_w$ greater than about 100,000 g/mole, preferably greater than about 200,000 g/mole, prior to crosslinking. Preferably the polyolefin has a relatively narrow molecular weight distribution (M$_w$/M$_n$) of less than about 4, e.g., less than about 3, prior to crosslinking.

In an aspect of the present disclosure, the polyolefin interpenetrated network can be prepared by mixing a precursor to a soft polyolefin network with a precursor to a rigid polyolefin network and then forming the network structures of the polyolefins. Prior to forming the network structures of the polyolefins, the mixture can be processed into various forms (e.g., films foams of various shapes and sizes), following with a thermal crosslinking reaction to form the polyolefin interpenetrated network.

For example, a precursor to a soft polyolefin network can be represented by formula (IV):

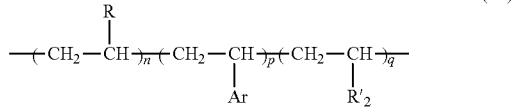

wherein (CH$_2$—CH(R)), R, (CH$_2$—CH(Ar)), Ar, n, and p represent the same groups as set out for formula (I) above, including all the various embodiments thereof, and R'$_2$ represents pendent thermally crosslinkable olefinic unit. That is the thermal crosslinking of R'$_2$ results in the —R$_2$—X—R$_2$— group of formula (I). A precursor to the rigid polyolefin network can be represented as precrosslinked form of formula (II) or a melted or solution form of formula (III). A process of making a polyolefin interpenetrated network can include mixing precursor of formula (IV) with a precursor to the rigid polyolefin network of formula (II) or (II) and, optionally processing the mixture into various forms (e.g., films foams of various shapes and sizes), followed by forming the network structures of the polyolefins, e.g., crosslinking the precursor of formula (IV) and formula (II) or crystallizing the polymer of formula (III).

In an embodiment of the present disclosure, the polyolefins of formula (I) and (II) are amorphous polymers and are cross-linked by heating the material in the bulk phase. For example, pendent styrene units on the polyolefin chain can be thermally cross-linked in the bulk phase by heating the material to temperatures of greater than about 220° C. This process fully cross-links the polyolefin. The polyolefin can also be thermally cross-linked by incorporating olefins having pendent vinyl groups to thermally react with one another or other vinyl groups pendent on the polyolefin chain to form a cross-linked polyolefin. Further, the cross-linked polyolefin of the present disclosure is preferably completely amorphous, i.e., the polymer has only one Tg transition and no detectable melting points (as determined by DSC described herein or equivalent equipment and procedures). The cross-linked soft polyolefin has a low Tg of less than about 10° C., and the crosslinked rigid polyolefin has a high Tg of more than about 50° C. Overall, the combination of a facile self-initiated thermal cycloaddition reaction (without any external reagent) and effective network formation without by-product (no purification step) provides a convenient and economic process to prepare the cross-linked polyolefin products individually and as a polyolefin interpenetrated network.

In another aspect of the present invention, the polyolefin in formula (III) is a semi-crystalline polymer with a melting temperature above 45° C. Upon heating above its Tm, the polymer becomes a molten liquid or soluble in solution with good processability. After cooling the polymer down to ambient temperature, some portions of the polymer chains form several crystalline domains, and the polymer becomes solid with strong mechanical strength. In practicing the present disclosure, the polyolefin interpenetrated network material can be formed by mixing a soft amorphous polyolefin (IV) with a precursor for rigid amorphous polyolefin (II) or a semi-crystalline polyolefin (III) in solution or melt, prior to crosslinking reaction. The homogeneous mixture can be processed into various forms, including film, fiber, pellet, and powder, with dense or porous morphology. By heating the mixture in the bulk phase, the thermal crosslinking reactions take place in the individual soft and rigid polyolefin chains of formula (IV) and the precursor to formula (II), respectively, and also between soft and rigid polyolefin chains, to form a stable polyolefin interpenetrated network material, in which a soft polyolefin network (I) and a rigid polyolefin network (II) are interpenetrated and both polymers are uniformly distributed in the network structure.

Alternatively, the polyolefin interpenetrated network can be formed by mixing a soft amorphous polyolefin (IV), prior to crosslinking reaction, and a rigid semi-crystalline polyolefin thermoplastic (III) in solution or melt. After processing the homogeneous mixture into various forms, including film, fiber, pellet, and powder, with dense or porous morphology, following with thermal crosslinking reaction of soft amorphous polyolefin (IV) in the bulk phase, the polyolefin blend is cooled down to ambient temperature. During this cooling process, the thermoplastic polyolefin thermoplastic melt (III) is partially crystallized to form the solid polymer network with a semi-crystalline morphology. Thus, the resulting polyolefin blend exhibits a stable polyolefin interpenetrated network material with two polymer chains interpenetrated and uniformly distributed in the network structure.

Polyolefin is an important class of commercial polymers and since they are prepared from petroleum downstream products, they exhibit many similar physical properties with the major components in crude oils. They are also inexpensive polymeric material, with a large production capacity around the world. The semi-crystalline polyolefin thermoplastic in formula (III), including low density polyethylene (LDPE), linear low density polyethylene (LLDPE), high density polyethylene (HDPE), isotactic polypropylene (i-PP), and syndiotactic polystyrene (s-PS) homo- and copolymers, are commonly used in various applications. However, the individual soft and rigid cross-linked polyolefins represented by formula (I) and (II), respectively, are not in use, despite the advantages of cross-linking the polymer structure, e.g., increasing temperature stability and resistance to electrical discharge, solvents, creep, and stress-cracking.

Rather, many cross-linked polyolefins are based on polyethylene (PE) and ethylene/propylene/diene elastomer (EPDM) polymers. The common cross-linking processes, including high energy irradiation (γ-rays and electron beams), peroxide-induced radical reactions, and silane-moisture cure mechanisms, are not particularly suitable in high alpha-olefin polymers. This is due to the inherent difficulties that the polymer backbone exhibits prompt degradation under free radical conditions, and catalyst poisoning during the transition metal mediated copolymerization of the cross-linkable silane-containing comonomers. In addition, most of the cross-linked polyolefin products do not have a complete network structure. That is, the gel content (insoluble fraction after solvent extraction) is generally below 90%.

Recently, we have reported an effective bulk (solid state) cross-linking process (Lin et. al., *Macromolecules* 2009, 42, 3750), involving a polypropylene (PP) copolymer that contains a few percentage of pendent styrene groups. Under elevated temperature (>160° C.), the pendent styrene units spontaneously engage in regiospecific [2+4] inter-chain cycloaddition reactions between two adjacent styrene units to form a complete 3-D network, even with a very low concentration of styrene units. Under the solid state condition, with highly entangled polymer chains and facile coupling reaction, offers convenient crosslinking chemistry. In addition, this self cross-linking process can result in a complete crosslinked polypropylene network with high purity and essentially free of contaminants.

Preferably, the cross-link density and hydrocarbon affinity of the polyolefins of the present disclosure are optimized such that the cross-linked polyolefin absorbs a target hydrocarbon to the maximum extent for the particular application. For example, a lower cross-linking density results in higher degree of swelling. Polyolefins prepared from one or more alpha olefin monomers having a pendant hydrocarbon moiety, such as 1-octene and 1-decene, are similar to the petroleum downstream products in refining crude oil and have similar solubility parameters (oleophilic and hydrophobic properties) as the hydrocarbon components in crude oil. The use of aromatic monomers, e.g., styrenes, with the alpha olefin monomers can further increase the affinity of crude oil to the polyolefin.

The cross-linked polyolefins of the present disclosure can be prepared by any conventional means. In one aspect of the present disclosure, the polyolefin can be prepared by a conventional Ziegler-Natta catalyst followed by thermal cross-linking. Scheme 1 illustrates an example synthesis of a thermally cross-linkable soft polyolefin, 1-decene/divinylbenzene (D-DVB) copolymers (a).

the four phenyl protons determine the vinyl/phenyl mole ratio, which is near unity. The experimental results confirm the mono-enchainment of DVB comonomers in forming the processible D-DVB copolymer (a).

In preparing polyolefin interpenetrated network, the resulting soft D-DVB copolymer (a) was mixed with a rigid polyolefin, such as semi-crystalline LLDPE copolymer (b), in solution or melt. The mixture was then processed to form various shape and size products (c), including films and foams with open porous morphology. Upon thermal heating (>220° C.) and then cooling down to ambient temperature, the formed product becomes a completely insoluble inter- Scheme 1: Synthesis of an interpenetrated x-D-DVB/LLDPE network.

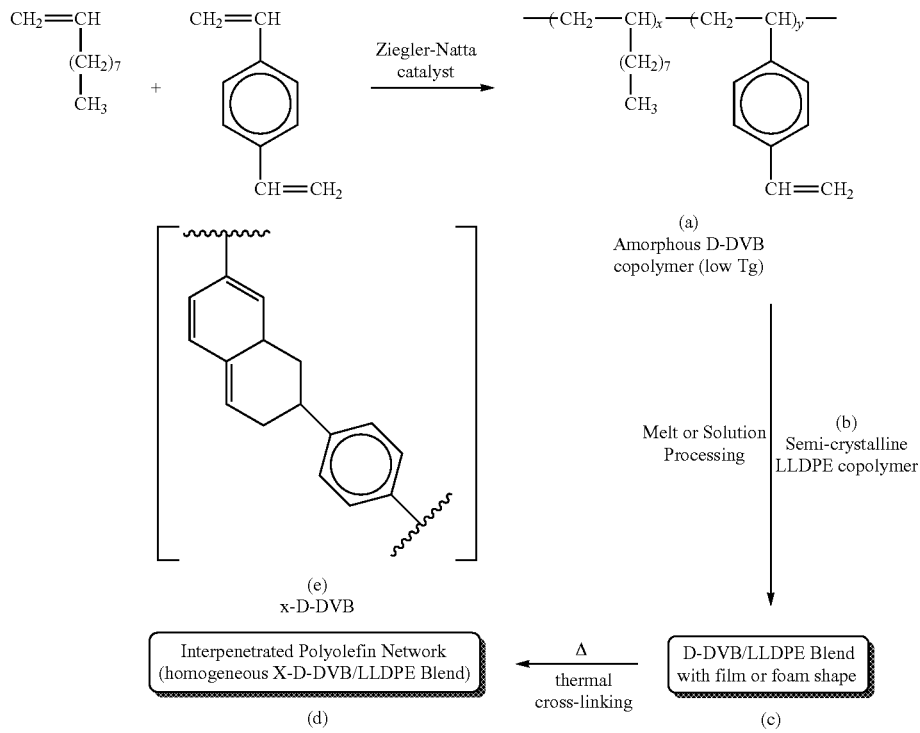

Figure 2:
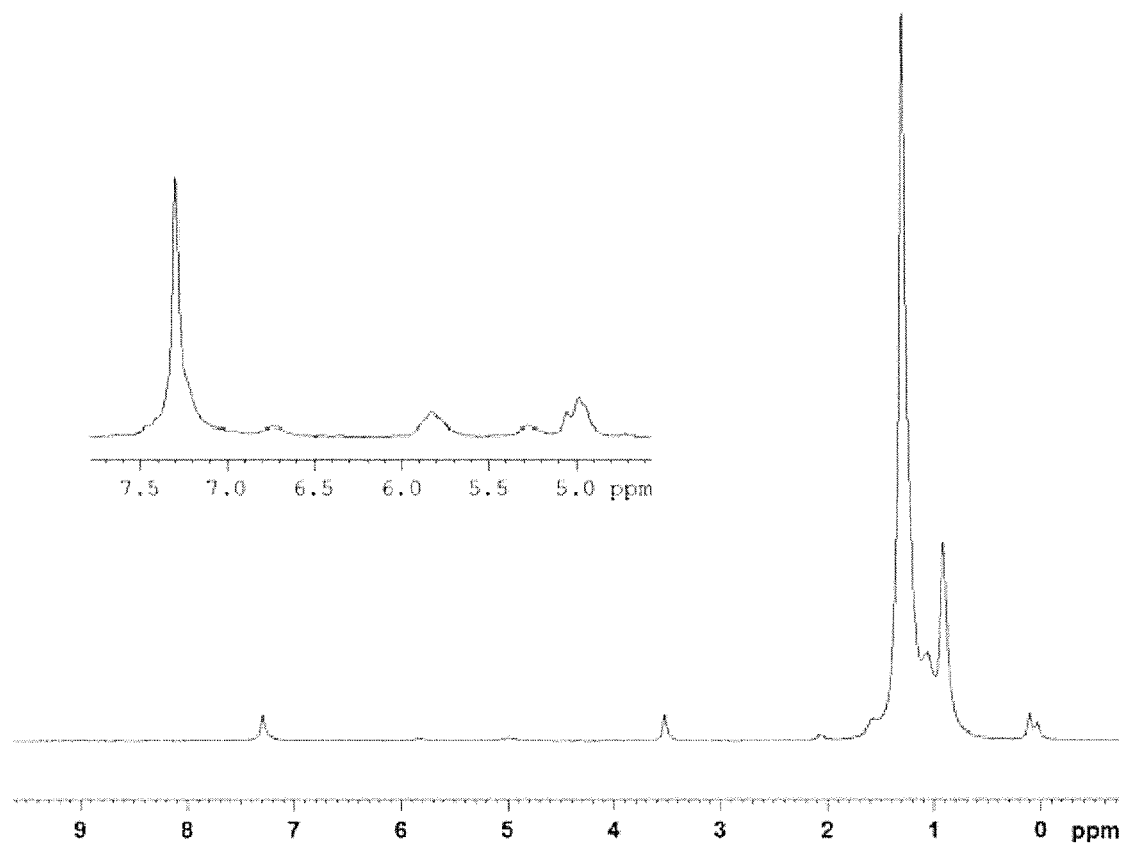
FIG. 2 shows the $^1$H NMR spectrum of a soft D-DVB copolymer containing 4 mol % of mono-enchained DVB units according to an embodiment of the present disclosure. (inset: expansion of the olefinic region to show mono-enchainment mode of DVB units)

In this scheme the cross-linkable polyolefin is prepared using a heterogeneous Ziegler-Natta catalyst (i.e. $TiCl_3$ (AA)/$AlCl_2Et$; where AA represents an activated by aluminum metal). This traditional Ziegler-Natta catalyst shows effective incorporation of 1-decene monomers and mono-enchainment of DVB at ambient temperature to form poly (1-decene-co-DVB) copolymer with high molecular weight ($M_w$>330,000 g/mol). As shown in Table 1, the high D-DVB copolymers, containing a broad range of DVB cross-linker units (up to 4 mol %), have been prepared without any detectable cross-linking reaction. The resulting D-DVB copolymers are completely soluble in common organic solvents, such as hexane and toluene. FIG. 2 shows the $^1H$ NMR spectrum of a D-DVB copolymer containing 4 mol % of DVB units. In addition to a chemical shift at 0.8 ppm, corresponding to $CH_3$ in the 1-decene units, and a band between 0.9 and 1.7 ppm, corresponding to $CH_2$ and CH in the polymer backbone, there are three bands around 5.2 and 5.7 ppm ($CH=CH_2$) and 6.7 ppm ($CH=CH_2$); and an aromatic proton band between 6.9 and 7.4 ppm ($C_6H_4$). The integrated intensity ratio between all three vinyl protons and penetrated polyolefin network material (d) that contains two independent networks, including a thermally-crosslinked x-D-DVB network and a semi-crystalline LLDPE network with both polymer chains intertwined and more or less uniformly distributed in the whole interpenetrated network structure (see, e.g., FIG. 1B). These polyolefin interpenetrated networks show dramatic improvement in absorption kinetic for viscous hydrocarbons and complex crude oils.

Both processing and thermal crosslinking reaction can happen in one step. Heat treatment is usually part of the processing procedure, the crosslinked x-D-DVB network structure (e) was formed by engaging in a Diels-Alder [2+4] inter-chain cycloaddition reaction between two pendent styrene units in the adjacent D-DVB polymer chains. This solid-state crosslinking reaction is very effective and without by-product, which eliminates the need for expensive solution-removal of hydrocarbon-soluble fraction shown in many conventional processes, in which the crosslinking reactions were usually carried out in dilute solutions with considerable amount of intra-chain coupling reaction. On the other hand, the mobile LLDPE polymer chains in solution or melt spontaneously form a strong and tough network structure during solvent evaporation or cooling, respectively. Some portion of LLDPE polymer chains form crystalline domains (physical crosslinkers) for creating an independent but intertwined network structure.

Thus, for the application of recovering crude oil from the environment such as crude oil in an open water environment, the soft polyolefin network, e.g., a x-D-DVB, should be lightly crosslinked, and the rigid polyolefin network, e.g., a semi-crystalline LLDPE copolymer, should have a Tm greater than ambient conditions but low enough for low crystallinity, such as a low as about 50° C., and a low degree of crystallinity, such as low as about 10%.

The combination of strong affinity of the oil to the olefinic monomers, most amorphous morphology, and high free volume due, in part, to the use of relatively long chain olefins in x-D-DVB, which form branched pendant groups from the main polymer chain, and light cross-linking, allow oil diffusion in such a matrix with fast kinetics. Such an x-D-DVB/LLDPE interpenetrated polyolefin network material can rapidly expand its matrix and achieve high oil absorption capacity and retention. In this embodiment, the oil molecules are captured inside the polymer matrix, with minimal or even completely without water absorption. The resulting polyolefin/oil composition can float on the water surface with good stability even after long exposure to air, and with minimal re-bleeding of the absorbed oil under waves or during the recovery operation.

Use of polyolefin interpenetrated network can be applied directly to the top of the leaking well head or oil slick or on an oil contaminated shoreline to form a gel that floats and can be readily collected and removed to mitigate pollution of water and air by an oil spill.

During the oil absorption evaluation, the interpenetrated polyolefin network materials were contacted with various oils and pure hydrocarbons to show their oil absorption capability and kinetics. Since crude oil is predominantly a mixture of aliphatic and aromatic hydrocarbons with various molecular weights, and the exact molecular composition varies widely from formation to formation, we decided to examine a broad range of petroleum products, including some representative pure aliphatic and aromatic compounds, along with Alaska North Slope (ANS) crude oil that is composed of aliphatic hydrocarbons (65-75%) and aromatic hydrocarbons (15-20%), with the molecular size from $C_5$ to $C_{30}$, and some impurities. Table 4 shows the experimental results with ANS crude oil, and the following Tables 5, 7, 8, and 9 summarizes the experimental results with several individual aliphatic and aromatic hydrocarbons (i.e. hexane, cyclohexane, benzene, and toluene) and some common petroleum products (i.e. gasoline, petroleum, and diesel).

The method for measurement of absorption capacity was carried out by following the standard method (ASTM F726-06) using various oils. Typically, a piece of polymer around 0.2 g was put into gasoline. After a certain time after reaching equilibrium, the sample was picked up with tweezers and weighed on a balance. Oil absorption capacity was calculated by the weight ratio between the absorbed oil to the original dried material. In order to study swelling kinetics, the above measurements were carried out from time to time. In addition, the absorption study was also extended to the individual crude oil components, including alkanes (such as heptane), cycloalkanes (such as cyclohexane), and aromatic hydrocarbons (toluene and xylene), respectively.

Figure 3:
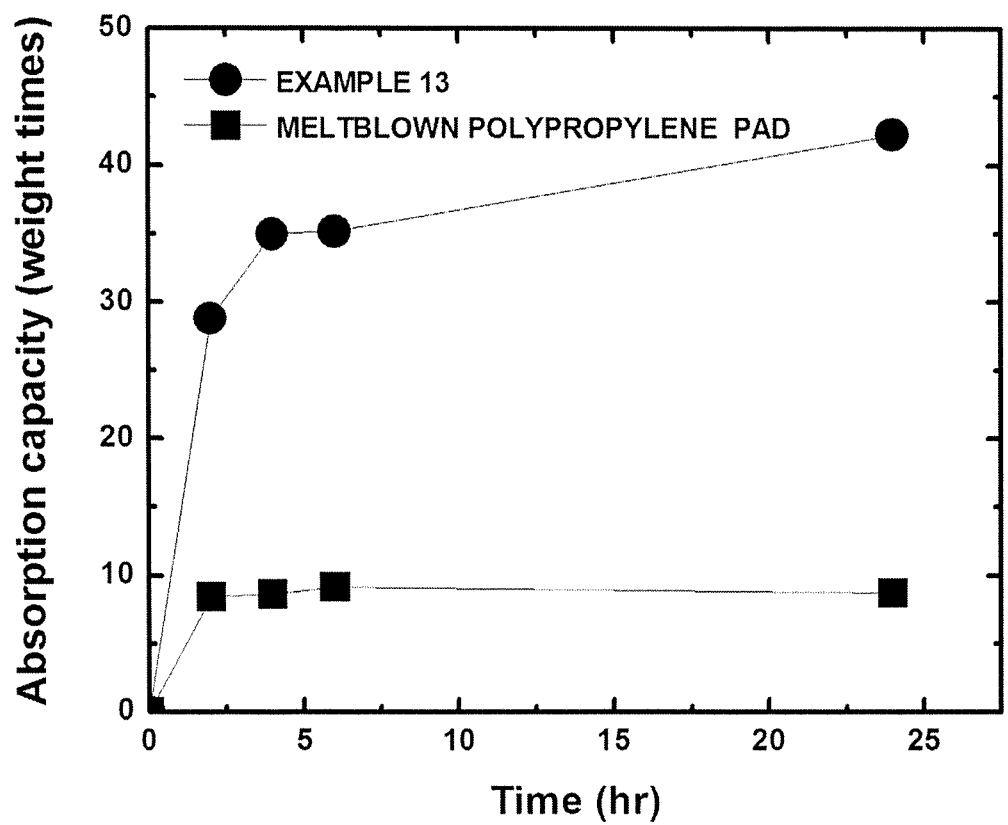
FIG. 3 is a chart showing ANS oil uptake vs. time for an x-D-DVB/LLDPE interpenetrated polyolefin network material (Example 13) compared to a commercially available meltblown polypropylene pad.

FIG. 3 compares the crude oil absorption performance between an x-D-DVB/LLDPE (1/1 weight ratio) interpenetrated polyolefin network material (Example 13) and a state-of-the-art meltblown polypropylene (PP) pad that is fabricated from a nonwoven fibrous PP textile with highly crystalline polymer structure and porous morphology (high surface area). The PP pad was obtained from Newpig Corporation in Pennsylvania and identified as PIG® White Oil-Only Mat Pads & Rolls. The samples were examined side-by-side for comparison using Alaska North Slope (ANS) crude oil. The meltblown PP pads (adsorption mechanism) show rapidly oil adsorption in their interstices by capillary action and saturated at the level about 10 times of weight uptake without any visible volume enlargement. The adsorption mechanism occurred on the PP fiber surfaces (not inside the matrix) which provides the material with fast kinetics but limited capacity. However, the weak oil-PP interaction results in some of the adsorbed oil re-bleeding under a slight external force.

In comparison, a polyolefin interpenetrated network of the present disclosure, e.g., a x-D-DVB/LLDPE interpenetrated polyolefin network, rapidly absorb ANS oil in its matrix, increasing its weight by more than 10 times within 10 minutes, reaching 30 times in 2 hours, and then reaching over 40 times after 24 hours. Its overall crude oil sorption capacity is superior (greater than about 4 times) to that of state-of-the-art meltblown PP pad. Furthermore, the x-D-DVB/LLDPE interpenetrated polyolefin network material (absorption mechanism) provides a stable oil storage environment to prevent oil from evaporating, emulsifying or spreading in other ways.

In addition to effective oil recovery, the resulting gel can be treated as crude oil, suitable for regular refining processes (distillation and cracking). In practicing an embodiment of the present disclosure, hydrocarbon can be separate from an oil loaded gel by heating the interpenetrated polyolefin network containing the at least one hydrocarbon. In one aspect of the present disclosure the oil loaded interpenetrated polyolefin network gel contains little to no water and has a composition similar to the original crude oil. During refining the gel, the minor component of the gel, which is the polyolefin interpenetrated network, can be thermally decomposed back to low molecular weight liquid hydrocarbon molecules without residue.

In another aspect, the interpenetrated polyolefin network materials of the present disclosure can be thermally decomposed back to low molecular weight hydrocarbons, e.g., monomers and other low molecular weight hydrocarbons, at elevated temperatures, e.g. from between about 300° C. to about 600° C. Preferably, the interpenetrated polyolefin network of the present disclosure can be completely thermally decomposed at temperatures of less than about 500° C., e.g., between about 300° C. to about 500° C., such that there is no residue after thermal decomposition of the interpenetrated polyolefin network. It is believed that the temperature used in the first refining or distillation step in a typical commercial oil refining process is greater than 600° C. The release of hydrocarbon and decomposition of the interpenetrated polyolefin network can advantageously be carried out in a typical commercial oil refining process such that the hydrocarbon-polyolefin composition can be treated in more or less the same manner as an oil feedstock in a refining process.

Figure 4:
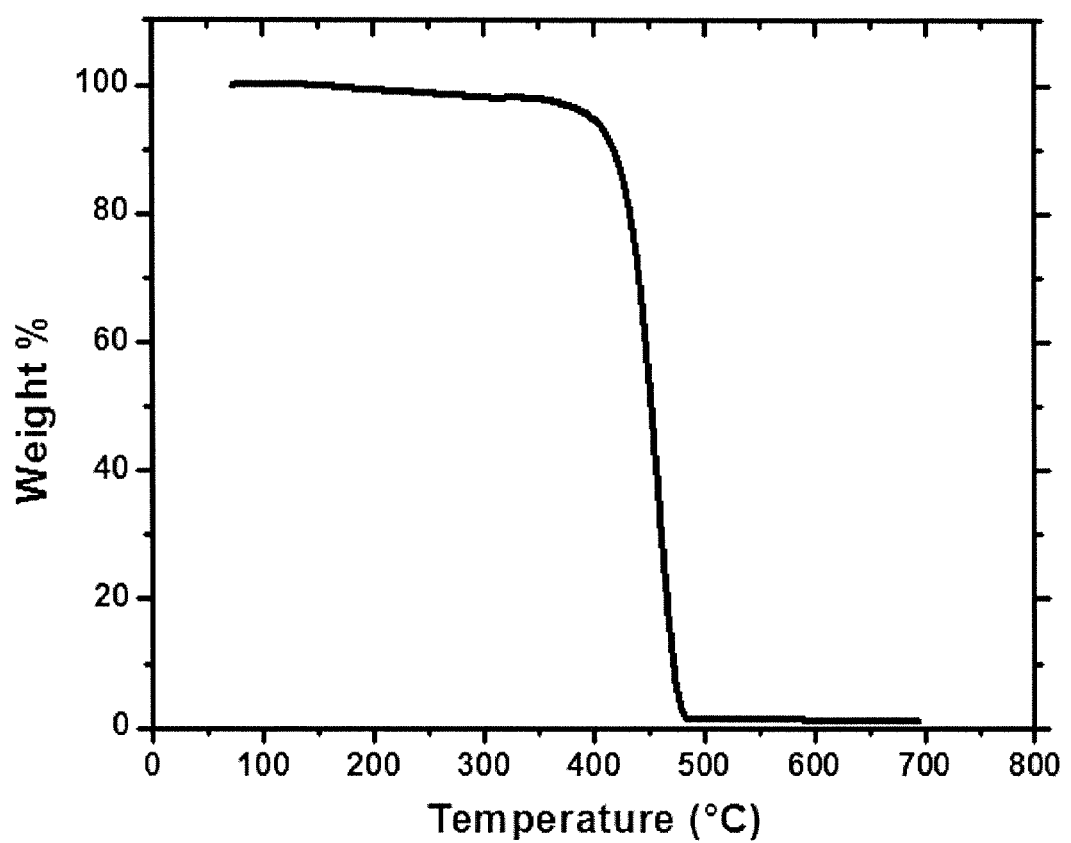
FIG. 4 shows a TGA curve of x-D-DVB/LLDPE interpenetrated polyolefin network material (Example 13) according to an embodiment of the present disclosure.

FIG. 4 shows a TGA (Thermogravimetric Analysis) curve of an x-D-DVB/LLDPE (1/1 weight ratio) interpenetrated polyolefin network material that can be thermally decomposed back to small hydrocarbon molecules without residue well below the typical crude oil refining temperature. Therefore, there would be little to no solid waste disposal.

In one embodiment of the present disclosure, the interpenetrated polyolefin network absorbs the hydrocarbon to form a gel (i.e., a hydrocarbon-polyolefin composition) that can be collected and decomposed by heat to release the hydrocarbon and substantially decompose the cross-linked polyolefin, preferably, into additional hydrocarbons. Preferably, the gel comprises the hydrocarbon in an amount that is at least 10 times the amount by weight of the interpenetrated polyolefin network material in the gel, e.g., wherein the amount by weight of hydrocarbon in the gel is ten times or more, such as at least 20, 30 or 40 times the weight of the polyolefin in the gel.

Figure 5:
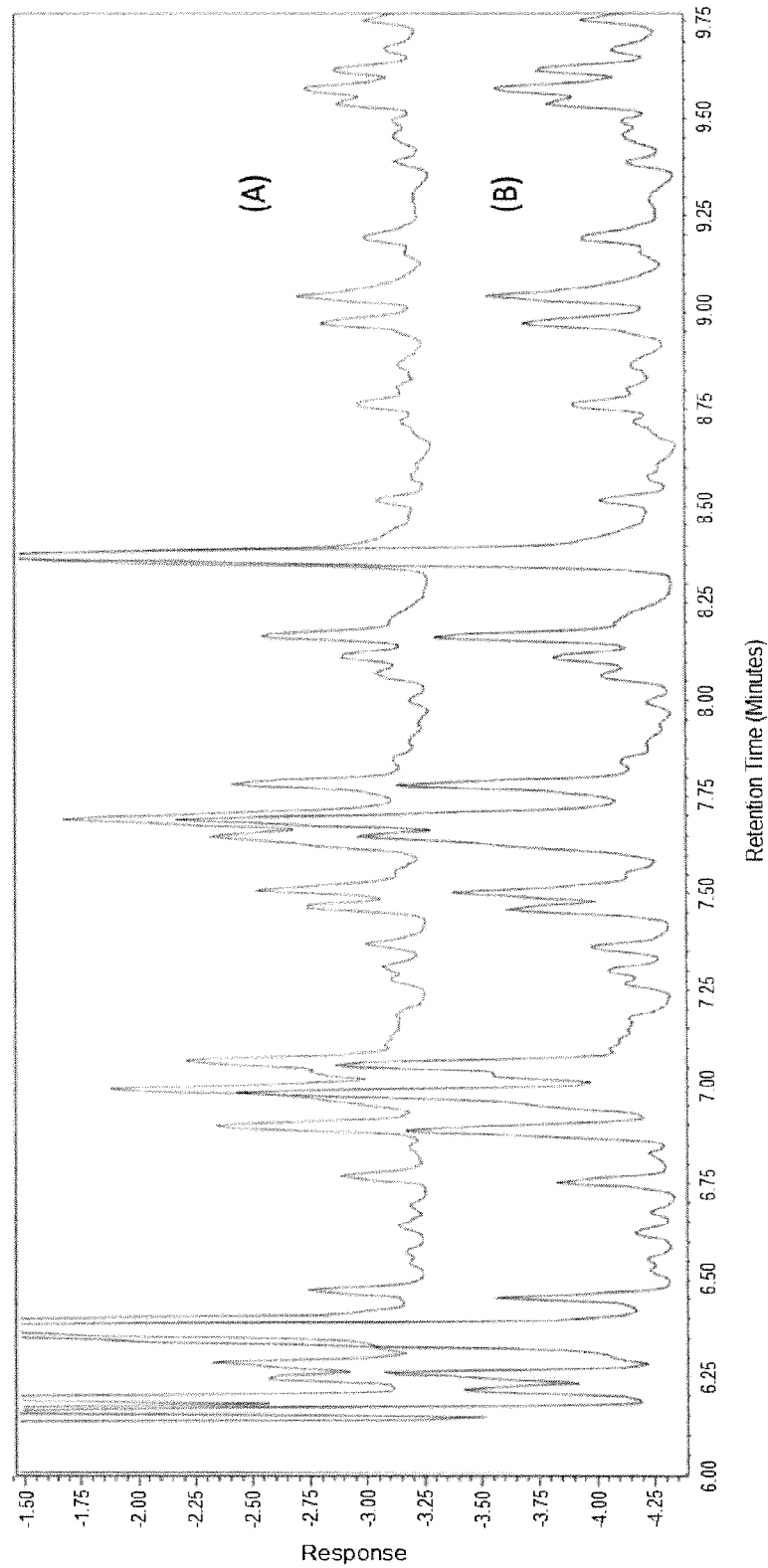
FIG. 5 compares GC-Mass spectra of (a) ANS crude oil and (b) recovered ANS crude oil from x-D-DVB/LLDPE gel (Example 13) which included about 3 wt % polyolefin and about 97 wt % ANS crude oil.

FIG. 5 compares GC-Mass curves between ANS crude oil and the recovered oil swelled gel that contains about 3 wt % of x-D-DVB/LLDPE (1/1 weight ratio) absorbent and 97 wt % of ANS crude oil. Two spectra are almost identical, indicating similar chemical composition and weight distribution among all components. Therefore, the x-D-DVB/LLDPE interpenetrated polyolefin network material absorbs all the hydrocarbon components in the ANS crude oil, and the resulting interpenetrated polyolefin network-hydrocarbon compositions are suitable for regular oil refining processes. Thus saving a portion of the spilled oil (an economically valuable natural resource), currently treated as pollutants to the environments and have the added advantage of minimizing disposal of solid waste and due to the recyclability and degradability of the interpenetrated polyolefin networks of the present disclosure.

Furthermore, polyolefin products are relatively inexpensive polymeric materials, with a large production capability around the world. It is estimated that the production cost of crosslinked polyolefins of the present disclosure can be below $2 per pound in large-scale industrial production. Thus, one pound of crosslinked polyolefin with 40 times absorption capacity can recover more than 5 gallons of the spilled oil (currently treated as a pollutant and waste) creating a product worth more than $7 (based on $50/barrel) and processable as regular crude oil.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Example 1

Synthesis of 1-Decene/Divinylbenzene (D-DVB) Copolymer and Crosslinking Reaction to Form a Soft Polyolefin Network The polymerization reaction was conducted in a 300 ml stainless autoclave equipped with a mechanical stirrer. The reactor was initially charged with 50 ml of toluene, 10 ml of 1-decene, and 0.5 ml of divinylbenzene (DVB) in an argon filled dry-box. The reactor was then sealed and then moved from the dry box and purged with nitrogen gas at 30° C. About 0.101 g of $TiCl_3(AA)$ and 1 ml of $AlCl_2Et$ in 3 ml of toluene were stirred for about 20 minutes and then introduced under nitrogen pressure to the reactor to initiate the polymerization. After about 3 hour, the reaction was terminated by adding 100 ml of dilute HCl solution in methanol to the reactor. The polymer was isolated by filtration and was washed completely with methanol and dried under vacuum for about 8 hours. About 5.44 g of D-DVB copolymer was obtained.

The copolymer was completely soluble in common organic solvents, including toluene and decalin. Its molecular structure was determined by a combination of $^1$H-NMR (Bruker AM-300 instrument in chloroform-d) and GPC measurements (Waters 1515 Isocratic HPLC pump with Waters 2414 refractive index detector). $^1$H-NMR spectrum shows the composition of 1-decene/divinylbenzene mole ratio=97.87/2.13, and the GPC curve indicates the copolymer has a weight average molecular weight of about 450 Kg/mol and a polydispersity index ($M_w/M_n$) of about 3.5.

To examine the cross-linking reaction, the resulting D-DVB copolymer was divided into ½ inch size particles and was heated in an oven at about 220° C. for about 2 hours to obtain the cross-linked samples. The resulting cross-linked 1-Decene/Divinylbenzene copolymer (x-D-DVB) was subjected to a vigorous solvent extraction by refluxing toluene for 36 hours to remove any soluble fraction that was not fully cross-linked into the network structure. After drying at 120° C. in vacuum for 8 hours, the insoluble x-D-DVB fraction was weighed to determine the gel content. The gel content is a measure of the percent that the copolymer is cross-linked and is determined by dividing the weight of the dried and extracted insoluble x-D-DVB fraction over the weight of the dried D-DVB sample prior to crosslinking. The results show almost the same weight between the dried and extracted insoluble x-D-DVB fraction and the dried D-DVB sample prior to crosslinking, indicating that the x-D-DVB copolymer is fully cross-linked, i.e., has a gel content of almost 100%.

Examples 2-5

Additional Synthesis of D-DVB Copolymers and Crosslinking Reaction to Form Soft Polyolefin Networks According to Formula I A series of samples were prepared in essentially the same procedure as described in Example 1. Polymerization for Examples 2-5 were carried out in 300 ml stainless autoclave equipped with mechanical stirrer. The same qualities of toluene, catalyst, co-catalyst, and 1-decene, were introduced into the reactor as described for Example 1, except a gradually decreasing divinylbenzene content (0.3, 0.2, 0.05, 0.02 ml) was used for Examples 2-5, respectively. The decreasing amount of divinylbenzene used in Examples 2-5 decreases the cross-linking density of the samples. After certain reaction time, the reactions were terminated by adding 100 ml of dilute HCl solution in methanol. The polymers were isolated by filtration and were washed completely with methanol and dried under vacuum for about 8 hours. The molecular structures of the copolymers were determined by a combination of $^1$H NMR measurements (Table 1). Samples of the resulting D-DVB copolymers were heated at about 220° C. in vacuum oven for about 2 hours to obtain cross-linked x-D-DVB samples. The gel content was determined in the manner described in Example 1 and the results are provided in Table 1.

TABLE 1

Summary of 1-decene/divinylbenzene copolymerization and oil absorption of the resulting crosslinked x-D-DVB copolymers.

| Example No. | Reaction Conditions | | | Copolymerization Results | | | |
|---|---|---|---|---|---|---|---|
| | 1-Decene (mL) | DVB (mL) | Temp/Time (° C./hr.) | 1-Decene (mol %) | DVB (mol %) | Yield (%) | Cross-linking (%) |
| 1 | 10 | 0.5 | 25/3 | 97.87 | 2.13 | 69 | 100 |
| 2 | 10 | 0.3 | 25/3 | 97.90 | 2.10 | 90 | 100 |
| 3 | 10 | 0.2 | 25/3 | 98.07 | 1.93 | 95 | 100 |
| 4 | 10 | 0.05 | 25/1 | 99.34 | 0.66 | 84 | 100 |
| 5 | 10 | 0.02 | 25/1 | 99.57 | 0.43 | 92 | 100 |

Examples 6-11

Study of Linear Low Density Polyethylene Polymers for Rigid Polyolefin Networks According to Formula III A series of commercial linear low density polyethylene (LLDPE), i.e. ethylene/1-octene copolymers with narrow molecular weight and composition distributions prepared by homogeneous metallocene catalyst, were used as the rigid polyolefin network in the interpenetrated polyolefin network (see, e.g., FIG. 1). The LLDPEs were analyzed by $^1$H-NMR, FTIR, and DSC spectroscopies to determine their molecular structure and semi-crystalline morphology. The results are summarized in Table 2. In the $^1$H NMR spectrum recorded on a Bruker (AVANCE300) at 110° C. in $d_4$-tetrachloroethane solvent, the chemical shift at 0.90 and 1.27-1.3 ppm, corresponding to side chain $CH_3$ groups and main chain $CH_2$ groups, respectively, were used to determine the side chain concentration. All FTIR spectra of LLDPE copolymers show several characteristic peaks at 2916 $cm^{-1}$ (asymmetric $CH_2$ stretching), 2848 $cm^{-1}$ (symmetric $CH_2$ stretching), 1460 $cm^{-1}$ ($CH_2$ bending, amorphous) and peaks at 720 $cm^{-1}$ ($CH_2$ rocking in amorphous domains). Thermal properties (Tm, heat of fusion, and crystallinity) were examined by Differential scanning calorimetry (TA DSC-Q100) at 10° C./min in second heating cycle. DSC curves of these LLDPE samples show systematically decrease in melting temperature and heat of fusion with the increase of side chain concentration. The side chains interfere with the PE chain folding crystallization process. Thus, as the number of side chains increases, the LLDPE material exhibits a lower density, lower melting temperature, and lower overall crystallinity.

TABLE 2

Molecular Structure and Physical Properties of Several LLDPE Copolymers

| Example no | Side chain (mol %) | Density (g/cm$^3$) | Melting temp. (° C.) | Softening temp. (° C.) | Crystallinity (%) |
|---|---|---|---|---|---|
| 6 | 4.3 | 0.909 | 106 | 95 | 36 |
| 7 | 5.1 | 0.897 | 95 | 78 | 28 |
| 8 | 7.4 | 0.875 | 75 | 56 | 20 |
| 9 | 8.4 | 0.870 | 55 | 43 | 18 |
| 10 | 8.9 | 0.868 | 55 | 46 | 16 |
| 11 | 9.4 | 0.865 | 47 | 32 | 16 |

TABLE 3

Hydrocarbon Absorption Capacity of LLDPE Copolymers

| Example no | Heptane | Toluene | Gasoline | Diesel |
|---|---|---|---|---|
| 6 | 0.06 | 0.21 | 0.11 | 0.02 |
| 7 | 0.91 | 0.43 | 0.35 | 1.71 |
| 8 | 1.51 | 2.25 | 2.12 | 2.75 |
| 9 | 1.78 | 5.60 | 2.63 | 7.14 |
| 10 | 7.57 | 11.7 | 7.74 | 21.2 |
| 11 | 18.6 | 27.1 | 18.7 | 36.4 |

To choose an optimized LLDPE copolymer for fabricating the polyolefin interpenetrated network, we first examined their hydrocarbon absorption capacity using 4 common refined oil products, including heptane, toluene, gasoline, and diesel, by following ASTM F716-09 (type II loose absorbent) procedure. The LLDPE sample was melt-compressed into film with 0.3 mm thickness. Typically, a piece of LLDPE film with specific weight ($W_1$) was put into a graduated cylinder. Add 100 times of oil, then capped with a stopper. After 2 hours at ambient temperature, free oil was poured out of the graduate cylinder and weight ($W_2$) of absorbed material was determined. Hydrocarbon absorption capacity (A) was calculated by the weight ratio between the absorbed oil ($W_2-W_1$) to the originally unabsorbed material ($W_1$), using the equation A (g/g)=($W_2-W_1$)/$W_1$. Table 3 shows the comparative hydrocarbon absorption results for six LLDPE samples. Evidently, the hydrocarbon absorption capacity of LLDPE copolymer is reversely proportional to its density, melting temperature, and crystallinity; that is higher density, melting temperature, and crystallinity lower absorption capacity. Example 11 shows the LLDPE copolymer with a lowest density and melting temperature, which also shows the best hydrocarbon absorption performance. However, the LLDPE copolymer with further reduction of density, melting temperature, and crystallinity results in soluble polymer in hydrocarbons, which is not suitable for serving as the absorbent. Thus, we decided to use LLDPE copolymer (Example 11) in the preparation of interpenetrated polyolefin network.

Examples 12-17

Preparation of x-D-DVB/LLDPE Interpenetrated Network Materials and Evaluation of ANS Crude Oil Absorption In the fabrication of x-D-DVB/LLDPE interpenetrated network material, we used two D-DVB copolymers (Examples 3 and 5), containing 1.93 and 0.43 mol % DVB cross-linker units, respectively, to form the soft polyolefin network and LLDPE copolymer of Example 11 for the rigid network. Typically, the D-DVB copolymer was dissolved in toluene and then mixed with LLDPE (20% in toluene) with different weight ratios under an elevated temperature condition to form a homogenous mixture. The homogeneous mixture was solution casted into films and dried under 120° C. oven condition in air for 15 min, then cooled down to ambient temperature. During the solvent evaporation process, the DVB units located along the D-DVB polymer chains engage in thermal cycloaddition reaction to form a cross-linked x-D-DVB network structure. In addition, the interpenetrated LLDPE polymer chains (now presented in the x-D-DVB polymer network) crystallized during the cooling process. The thus formed small crystallites in LLDPE serve as physical cross-linkers to prevent dissolution of LLDPE polymer in hydrocarbon media. Thus, this x-D-DVB and LLDPE binary combination results in a morphology with two interpenetrated polymer networks. The polymer chains in the x-D-DVB network and the semi-crystalline LLDPE network are intertwined and homogeneously distributed in the interpenetrated polyolefin network structure (see e.g., FIG. 1B).

With the presence of semi-crystalline LLDPE thermoplastic, the resulting x-D-DVB/LLDPE material is tough and not sticky and has the mechanical strength to form various structures and morphologies (i.e. films, foams, powders, etc.). The handling properties of the polyolefin interpenetrated network can be easily tuned by the mixing ratio between D-DVB and LLDPE copolymers, as well as the DVB (crosslinker) content in D-DVB copolymer.

To assess factors that control crude oil absorption capacity and kinetics, we prepared several x-D-DVB/LLDPE interpenetrated network materials with various compositions and morphologies and evaluated their performance with Alaska North Slope (ANS) crude oil.

Table 4 compares ANS oil absorption capacity between two sets (Examples 12-14 and Examples 15-17) of x-D-DVB/LLDPE interpenetrated network samples using two x-D-DVB copolymers with 1.93 and 0.43 mole % DVB cross-linker contents, respectively, and the corresponding individual x-D-DVB and LLDPE copolymer samples. Except two soft (somewhat sticky) x-D-DVB samples (Examples 3 and 5), all samples were processed into film forms, with the thickness between 0.20 and 0.30 mm, and the absorption tests were conducted under similar experimental conditions at 25 or 0° C., following ASTM F716-09 (type II loose absorbent procedure). The absorption capacity was determined by measuring the weight ratio $W_t-W_0/W_0$ between the absorbed oil to the original dried absorbent, wherein $W_0$ is the initial weight of the absorbent sample and $W_t$ is the total weight of absorbent-hydrocarbon gel after 24 hours.

TABLE 4

ANS Oil Absorption Capacity of Several x-D-DVB/LLDPE Interpenetrated Network Materials and the Corresponding x-D-DVB and LLDPE Copolymer Samples.

| Example No. | x-D-DVB/ LLDPE (weight ratio) | DVB content in D-DVB copolymer (mole %) | ANS Oil absorption Capacity 25° C. | 0° C. |
|---|---|---|---|---|
| 12 | 3:1 | 1.93 | 22 | 30 |
| 13 | 1:1 | 1.93 | 42 | 37 |
| 14 | 1:3 | 1.93 | 37 | 45 |
| 15 | 3:1 | 0.43 | 28 | 20 |
| 16 | 1:1 | 0.43 | 47 | 32 |
| 17 | 1:3 | 0.43 | 36 | 37 |
| 3 | x-D-DVB | 1.93 | 6.6 | — |
| 5 | x-D-DVB | 0.43 | 7.3 | — |
| 6 | LLDPE | — | 0.16 | — |
| 7 | LLDPE | — | 1.71 | — |
| 8 | LLDPE | — | 1.63 | — |
| 9 | LLDPE | — | 1.64 | — |
| 10 | LLDPE | — | 3.19 | — |
| 11 | LLDPE | — | 10.2 | — |

Comparing the ANS crude oil absorption results, all x-D-DVB/LLDPE interpenetrated network samples show significantly better oil absorption performance (greater than 2 times) than the corresponding individual x-D-DVB (soft network) and LLDPE (rigid network). Further, the crude oil absorption of the polyolefin interpenetrated networks was significantly better than an additive effect from the individual components.

FIG. 3 shows a typical absorption curve (absorption capacity vs. time) for Example 13 that has a x-D-DVB/LLDPE interpenetrated network material with 1/1 weight ratio and 1.93 mol % DVB cross-linker content in the x-D-DVB network. This polyolefin interpenetrated network exhibits very fast absorption kinetics, almost reaching to the saturation level in 2-3 hours. After contacting with ANS oil for 24 hours, this x-D-DVB/LLDPE interpenetrated network material reaches an absorption capacity of 42 and 37 times at 25 and 0° C., respectively. It is also very interesting to see Example 14, with ⅓ weight ratio in the same set of x-D-DVB/LLDPE interpenetrated network material, reaches to 45 times oil absorption capacity at 0° C. (icy condition). On the other hand, Example 12 with 3/1 soft and rigid weight ratio shows significantly less absorption capacity, which may be associated with the recovery of the resulting polymer-ANS oil gel. This sample after absorbing a large quantity of ANS oil becomes too soft to fully recover by tweezer. Similar experimental results were observed in the other set (Examples 15-17) of x-D-DVB/LLDPE interpenetrated network materials, which involves x-D-DVB copolymer with 0.43 mol % DVB cross-linker units and the same three different compositions 3/1, 1/1, and 1/3 weight ratios between soft and rigid polymer networks. Again, Examples 16 and 17 with 1/1 and 1/3 weight ratios show good absorption capacity and fast kinetics at 25 and 0° C., and Example 15 after fully absorbing ANS oil with large volume expansion becomes too soft to pick up by tweezer.

FIG. 5 compares GC-Mass spectra of Example 13 after fully absorbing ANS oil and ANS oil itself. During the measurement, the polymer-ANS oil gel mixture was pyrolyzed by rapid heating to 650° C. (60° C./s) to decompose the polyolefin polymer into small molecules before GC-Mass measurement. Remarkably, the two curves are almost indistinguishable. The curves demonstrate that the by heating a gel comprising an interpenetrated polyolefin network containing ANS, the release of hydrocarbons from such a gel has essentially the same ANS oil mixture profile. Since the polymer content in the gel mixture is less than 3 weight percentage, the GC-Mass spectrum is dominated by the composition of ANS oil.

Further as demonstrated in FIG. 4, the polyolefin interpenetrated network (Example 13) can be completely thermally decomposed to liquid hydrocarbon (oil) molecules. Weight loss versus temperature was recorded in a thermogravimetric analyzer (TA-TGA Q500) under argon atmosphere, with sample weight about 20 mg and heating rate of 20° C./min. After about 500° C., the TGA shows no residue remaining from the thermal decomposition of the polyolefin interpenetrated network.

The combination of thermal degradation property of the polyolefin interpenetrated network and its selective oil absorption capability (without water) is very unique, which offers an oil spill recovery process without secondary pollution due to the disposal of recovered oil/water mixtures and solid wastes. It saves the environment and nature resource.

Example 18-22

Synthesis and Evaluation of 1-Octene/Styrene/DVB (OS-DVB) Terpolymers and Soft Polyolefin Networks The following examples 18-22 show how to make additional soft polyolefin networks according to formula I. The polymerization of 1-octene/styrene/divinylbenzene (OS-DVB) terpolymer was conducted in a 300 ml stainless autoclave equipped with a mechanical stirrer. In a typical reaction (Example 18), the reactor was initially charged with 50 ml of toluene, 5 ml of 1-octene (31.9 mmol), 5 ml of styrene (43.3 mmol), and 0.2 ml of divinylbenzene (DVB) (1.4 mmol) in an argon filled dry-box. The reactor was then sealed and then moved from the dry box and purged with nitrogen gas at 30° C. About 0.101 g of $TiCl_3(AA)$ and 1 ml of $AlCl_2Et$ in 10 ml of toluene were stirred for about 20 minutes and then introduced under nitrogen pressure to the reactor to initiate the polymerization. After about 3 hours, the reaction was terminated by adding 100 ml of dilute HCl solution in methanol to the reactor. The polymer was isolated by filtration and was washed completely with methanol and dried under vacuum for about 8 hours. About 2.79 g of OS-DVB terpolymer was obtained. The terpolymer was completely soluble in common organic solvents, including toluene and decalin. $^1$H-NMR spectrum shows the composition of 1-octene/styrene/divinylbenzene mole ratio=87.7/17.4/0.3, and the GPC curve indicates the terpolymer has a weight average molecular weight of about 330 Kg/mol and a polydispersity index ($M_w/M_n$) of about 2.1. Polymerization for Examples 19-22 were carried out with the same qualities of toluene, catalyst, co-catalyst, 1-octene, and styrene, except a gradually increasing divinylbenzene content (0.5, 1, 2.5, and 5 ml), respectively. The increasing amount of divinylbenzene used in the copolymerization increases the cross-linking density of the examples.

In examining the cross-linking reaction, the resulting terpolymer was divided into ½ inch size particles and was heated in an oven at about 220° C. for about 2 hours to obtain the cross-linked samples. The resulting cross-linked 1-Octene/Styrene/Divinylbenzene (x-OS-DVB) terpolymer was subjected to a vigorous solvent extraction by refluxing toluene for 36 hours to remove any soluble fraction that was not fully cross-linked into the network structure. After drying at 120° C. in vacuum for 8 hours, the insoluble x-OS-DVB fraction was weighed to determine the gel content. The gel content is a measure of the percent that the terpolymer is crosslinked and is determined by dividing the weight of the dried and extracted insoluble x-OS-DVB fraction over the weight of the dried OS-DVB sample prior to crosslinking. Evidently, all x-OS-DVB samples in Table 5 show no detectable soluble fraction, even in the terpolymer (Example 18) with only 0.3 mol % DVB units, indicating a very efficient thermal cross-linking reaction under a polymer melt state condition. The extensive chain entanglement among many polymer chains significantly enhances the inter-chain Diels-Alder [2+4] cycloaddition reaction between two pendent styrene units from adjacent polymer chains. The high molecular weight terpolymer with narrow molecular weight and composition distributions certainly also helps in achieving the complete network structure.

The absorption capacity data for the various cross-linked samples of Examples 18-22, respectively, in various hydrocarbons are summarized in Table 5. The absorption capacity was determined in the same manner as described in Examples 6-11.

TABLE 5

Synthesis and hydrocarbon absorption for several x-OS-DVB terpolymers[1]

| | Polymerization Results | | | | |
|---|---|---|---|---|---|
| Example no. | Monomer A/B/C[2] (ml) | Terpolymer [A]/[B]/[C][3] (mole ratio) | Yield (g) | $M_w$[4] (Kg/mol) | Gel[5] (%) |
| 18 | 5/5/0.2 | 82.3/17.4/0.3 | 3.07 | 330 | 100 |
| 19 | 5/5/0.5 | 79.3/20.2/0.5 | 3.76 | 410 | 100 |
| 20 | 5/5/1 | 78.4/20.7/0.9 | 3.94 | 420 | 100 |
| 21 | 5/5/2.5 | 76.3/22.3/1.4 | 4.02 | 460 | 100 |
| 22 | 5/5/5 | 74.1/24.0/1.9 | 4.56 | 520 | 100 |

| | Absorption capacity (weight ratio)[6] | | | | | | |
|---|---|---|---|---|---|---|---|
| Example no. | Gasoline | Petroleum | Diesel | Toluene | Hexane | Benzene | Cyclohexane |
| 18 | 41.3 | 40.3 | 41.1 | 47.1 | 42.8 | 40.7 | 43.5 |
| 19 | 21.1 | 19.6 | 20.0 | 22.7 | 20.4 | 19.8 | 22.0 |
| 20 | 13.7 | 11.6 | 11.9 | 11.6 | 11.9 | 14.1 | 14.1 |
| 21 | 6.41 | 6.28 | 6.39 | 6.24 | 5.62 | 5.59 | 7.02 |
| 22 | 5.45 | 5.34 | 5.40 | 4.75 | 5.10 | 5.21 | 5.80 |

[1]Polymerization condition: $TiCl_3(AA)/AlCl_2Et$ = 0.101 g/4 ml (25 wt % in toluene), 50 ml of toluene, 25° C. for 3 h; Cross-linking condition: 220° C for 2 h.
[2]A: 1-octene, B: styrene, and C: divinylbenzene.
[3]Determined by $^1$H NMR spectra.
[4]Measured by GPC with a standard polystyrene calibration curve.
[5]The gel content was determined from the toluene-insoluble part after Soxhlet extraction.
[6]Absorption time: 24 hours

Example 23-33

Synthesis and Evaluation of Styrene/p-Methylstyrene/DVB (S-p-MS-DVB) Terpolymers and Rigid Polyolefin Networks According to Formula II The following examples 23-33 show how to make rigid polyolefin networks according to formula II. A systematical series of styrene/p-methylstyrene/divinylbenzene terpolymerization reactions were conducted using $C_p$*$TiCl_3$/MAO metallocene catalyst. This $C_p$*$TiCl_3$/MAO metallocene catalyst shows effectively polymerization activities for styrenic monomers (i.e. styrene and alkyl-substituted styrene) and single enchainment of DVB monomer. It is also known that this catalyst system also prepares semi-crystalline syndiotactic polystyrene (s-PS) with high crystallinity and high molecular weight. In other words, the incorporated styrene units, located along the polymer chain, can easily form crystalline domains. Table 6 summarizes the experimental conditions and results. In Example 23, with only styrene monomer, the polymer formed is an s-PS polymer with high crystallinity ($\Delta H=33.49$ J/g) and high melting temperature ($T_m$ at 273° C.). As expected, a $T_g$ at 108° C. is also observed for the glass transition temperature of amorphous polystyrene domains, which is well above ambient temperature. The strategy to reduce crystallization of s-PS is to prepare styrene/p-methylstyrene (S-p-MS) copolymers. Both monomers are commercially available in large quantities with similar cost. The extra p-methyl groups randomly distributed along the copolymer chains can prevent the polymer crystallization. Evidently, the systematical increase of p-MS content in the copolymers, the crystallinity ($\Delta H$) and $T_m$ of S/p-MS copolymer are gradually reduced, while the Tg is almost constant. In Example 27, with almost equal amount of styrene and p-methylstyrene units, the S-p-MS copolymer is completely amorphous, with only one thermal transition ($T_g$ of about 105° C.) in the DSC curve. The composition of S-p-MS copolymer almost follows the comonomer feed ratio, indicating similar comonomer reactivity ratio that leads to the formation of random S-p-MS copolymer. This is a highly controlled copolymerization system, which allows us to move further to incorporate DVB crosslinker. As shown in Examples 30-33, we have prepared several S-p-MS-DVB terpolymers with single enchainment of DVB units and a broad range of DVB contents. The incorporated DVB concentration is also followed with the monomer feed, and all resulting S-p-MS-DVB terpolymers are soluble in common organic solvents, such as toluene. Overall, this $C_p$*$TiCl_3$/MAO mediated copolymerization reaction is very effective to prepare aromatic polymers with high molecular weight, high polymer yield (catalyst activity), and similar comonomer reactivity ratio among three styrenic comonomers (i.e. styrene, p-methylstyrene, and divinylbenzene).

TABLE 7

Summary of Hydrocarbon Absorption Capacity of Two x-S-p-MS-DVB Terpolymers.

| Example No. | Oil absorption capacity (g/g) | | |
|---|---|---|---|
| | Toluene | Diesel | ANS oil |
| 30 | 33.25 | 14.63 | 6.75 |
| 31 | 28.52 | 9.25 | 4.56 |

The corresponding thermally-crosslinked (x-S-p-MS-DVB) rigid networks were evaluated to understand their oil absorption capacity using three hydrocarbons, including toluene, diesel, and ANS oil, by following ASTM F716-09 (type II loose absorbent) procedure. It is not surprised to see a relatively high toluene absorption capacity in this x-S-p-MS-DVB material, both are aromatic compounds. However, the absorption capacities for diesel and ANS oil are significantly lower. Since the aromatic hydrocarbons content in diesel and ANS crude is only about 25% and 15-20%, respectively, we do not expect a high diesel and ANS oil absorption capacities in these dense aromatic network materials.

Examples 34-39

Preparation of x-OS-DVB/x-S-p-MS-DVB Interpenetrated Network Materials and Evaluation of ANS Crude Oil Absorption In the fabrication of x-OS-DVB/x-S-p-MS-DVB interpenetrated network material, according to FIG. 1A, we used an OS-DVB terpolymers (Example 18), containing 0.3 mol % DVB cross-linker units to form the soft polyolefin network and two amorphous S-p-MS-DVB terpolymers (Examples 30 and 31), respectively, for the rigid network. Typically, two terpolymers with different weight ratios were dissolved in toluene under ambient temperature condition to form a homogenous solution. The homogeneous mixture was casted into films and dried under 200° C. oven condition in air for 15 min, then cooled down to ambient temperature. During the solvent evaporation process, the DVB units located along both polymer chains engage in thermal

TABLE 6

Synthesis of Aromatic S/p-MS/DVB Terpolymers using Metallocene $C_p$*$TiCl_3$/MAO catalyst.

| | Polymerization Conditions[a] | | | Polymerization Results | | | |
|---|---|---|---|---|---|---|---|
| Example No. | S/p-MS/DVB (M/M/ml) | Temp/Time (° C./hr) | Yield (%) | S/p-MS/DVB[b] (mol %) | $T_g$[c] (° C.) | $T_m$[c] (° C.) | $\Delta H$ (J/g) |
| 23 | 1/0/0 | 25/0.5 | 60 | 100/0/0 | 108 | 273 | 33.49 |
| 24 | 0.9/0.1/0 | 25/0.5 | 63 | 86.6/11.4/0 | 101 | 247 | 19.94 |
| 25 | 0.7/0.3/0 | 25/0.5 | 68 | 72.1/27.9/0 | 105 | 211 | 15.22 |
| 26 | 0.6/0.4/0 | 25/0.5 | 65 | 61.4/38.6/0 | 106 | 192 | 1.79 |
| 27 | 0.5/0.5/0 | 25/0.5 | 69 | 50.2/49.8/0 | 105 | no | no |
| 28 | 0.3/0.7/0 | 25/0.5 | 63 | 31.1/68.9/0 | 107 | no | no |
| 29 | 0.1/0.9/0 | 25/0.5 | 68 | 11.8/88.2/0 | 109 | no | no |
| 30 | 0.5/0.5/0.05 | 25/1 | 94 | 50.0/49.5/0.5 | 106 | no | No |
| 31 | 0.5/0.5/0.1 | 25/1 | 92 | 49.5/49.4/1.1 | 107 | no | no |
| 32 | 0.5/0.5/0.2 | 25/1 | 90 | 49.6/48.1/2.3 | 107 | no | no |
| 33 | 0.5/0.5/0.3 | 25/1 | 90 | 48.6/47.8/3.6 | 108 | no | no |

[a]Solvent: 50 mL toluene.
[b]S: styrene; p-MS: p-methylstyrene; DVB: divinylbenzene cross-linker.
[c]$T_g$ and $T_m$ were determined by DSC measurements using TA DSC-Q100 calorimetry at 10° C./min in second heating cycle.

cycloaddition reaction to form the interpenetrated x-OS-DVB/x-S-p-MS-DVB network material with good mechanical strength.

To assess factors that control crude oil absorption capacity, we prepared two sets of x-OS-DVB/x-S-p-MS-DVB interpenetrated network materials with various compositions as shown in Table 8. All samples were processed into films with thickness in the range of 0.20-0.3 mm, and the absorption tests were conducted under similar experimental conditions using ANS crude oil at 25 or 0° C., following ASTM F716-09 (type II loose absorbent procedure). The absorption capacity was determined by measuring the weight ratio $W_t-W_0/W_0$ between the absorbed oil to the original dried absorbent, wherein $W_0$ is the initial weight of the absorbent sample and $W_t$ is the total weight of absorbent-hydrocarbon gel after 24 hours.

TABLE 8

Comparison of ANS Oil Absorption Capacity of Several x-OS-DVB/x-S-p-MS-DVB Interpenetrated Network Materials.

| Example No. | x-OS-DVB/ x-S-p-MS-DVB (weight ratio) | x-S-p-MS-DVB (source) | ANS Oil absorption Capacity | |
|---|---|---|---|---|
| | | | 25° C. | 0° C. |
| 34 | 3:1 | Example 30 | 36 | 37 |
| 35 | 1:1 | Example 30 | 33 | 32 |
| 36 | 1:3 | Example 30 | 28 | 30 |
| 37 | 3:1 | Example 31 | 30 | 28 |
| 38 | 1:1 | Example 31 | 27 | 28 |
| 39 | 1:3 | Example 31 | 24 | 25 |

Comparing the ANS crude oil absorption results, all x-OS-DVB/x-S-p-MS-DVB interpenetrated network samples show significantly better oil absorption performance than the corresponding individual x-OS-DVB soft network and x-S-p-MS-DVB rigid network (Table 7). After contacting with ANS oil for 2 hours, all IPN samples show significantly swelling with more than 20 times weight increase. The temperature effect between 25° C. and 0° C. is generally very small. Since the aromatic hydrocarbons content in ANS crude is only about 15-20%, it may also explain the reduction of oil absorption capacity in the aromatic-rich IPN materials (Examples 36 and 39). Comparing two sets (Examples 34-36 and Examples 37-39), using two rigid x-S-p-MS-DVB networks (Examples 30 and 31) with two different crosslinking densities, the first set with low cross-linking density shows significantly better performance.

Example 40-45

Synthesis and Evaluation of Ethylene/1-Octene/1,7-Octadiene Terpolymers

The following example shows how to make additional soft polyolefin networks. In a typical terpolymerization reaction (Example 40), in a dry Parr 300 ml stainless autoclave equipped with mechanical stirrer, 75 ml of toluene, 11.8 ml of 1-octene, 0.2 ml of 1,7-octadiene and 5 ml MAO solution (methylaluminoxane, 10 wt % in toluene) were mixed at 60° C. After purging with ethylene gas, about 1 µmol of rac-Me$_2$Si[2-Me-4-Ph(ind)$_2$ZrCl$_2$] catalyst diluted in 3 ml toluene was then syringed into the rapidly stirring solution under ethylene pressure to initiate the polymerization. After 3 minutes of reaction at 60° C. and under 220 psi pressure of ethylene gas, the polymer solution was quenched with methanol. The resulting product was washed with HCl/methanol (0.5M) and methanol each for 3 times, then vacuum-dried at 60° C. About 3.06 g of ethylene/1-octene/1,7-octadiene terpolymer was obtained with a catalyst activity of 61.2 Kg(PE)/mmol Zr/h. Before absorption measurements, the resulting polymer was subjected to a vigorous solvent extraction by refluxing toluene for 36 hours to remove any soluble fraction that was not fully cross-linked into the network structure. The soluble fraction was weight to calculate the data of gel content (insoluble fraction). As shown in Table 9, the resulting ethylene/1-octene/1,7-octadiene terpolymer polymer from this reaction was not completely cross-linked, with only 40% insoluble fraction. In addition, this terpolymer also exhibits a small degree of crystallinity.

A series of ethylene/1-octene/1,7-octadiene terpolymers were prepared in a manner similar, except various volumes of 1-octene and 1,7-octadiene (11.5 ml/0.5 ml, 11 ml/1 ml, 10 ml/2 ml, 8 ml/4 ml) for Examples 41-44 and 110 psi ethylene pressure for Example 45. Only the fully cross-linked polymers were subjected to oil absorption with a small piece of sample (about 0.5 g) at room temperature. In addition, the absorption study was also extended into the individual crude oil components, including alkanes (such as heptane), cycloalkanes (such as cyclohexane) and aromatic hydrocarbons (toluene and benzene). The absorption capacity data for the various crosslinked samples of Examples 42-45, respectively, in various hydrocarbons are summarized in Table 9. The cross-linked ethylene/1-octene/1,7-octadiene polyolefins can absorb between about 8 to about 29 times their weight with the refined aliphatic and aromatic hydrocarbons. However, the absorption capacity is significantly reduced with ANS crude oil having complex compositions.

TABLE 9

Synthesis and oil absorption evaluation of ethylene/1-octene/1,7-octadiene terpolymers.

| | Polymerization condition | | | | |
|---|---|---|---|---|---|
| Example No. | 1-octene (ml) | 1,7-octadiene (ml) | Yield (g) | Cat Activity (Kg/mmol · h) | Gel % |
| 40 | 11.8 | 0.2 | 3.06 | 61.2 | 40 |
| 41 | 11.5 | 0.5 | 4.24 | 80.5 | 76 |
| 42 | 11 | 1 | 4.74 | 94.8 | 100 |
| 43 | 10 | 2 | 5.38 | 108 | 100 |
| 44 | 8 | 4 | 9.51 | 190 | 100 |
| 45 | 11 | 1 | 7.94 | 95.2 | 100 |

| Example | Absorption capacity (weight ratio) | | | | |
|---|---|---|---|---|---|
| No. | Toluene | Heptane | Cyclo-hexane | Gasoline | ANS oil |
| 42 | 19.5 | 17.4 | 23.2 | 18.3 | 8.3 |
| 43 | 15.3 | 11.1 | 19.7 | 13.5 | 6.5 |
| 44 | 10.2 | 8.3 | 11.8 | 10.3 | 3.5 |
| 45 | 22.4 | 18.1 | 29.1 | 17.1 | 7.1 |

The disclosure provides polyolefin interpenetrated network effective for absorbing hydrocarbons and examples for their preparation, which includes polymerization using conventional Ziegler-Natta catalyst followed by thermal cross-linking reactions. The combination of oleophilic and hydrophobic properties with porous morphology, high free volume, and high surface area provides the cross-linked polyolefins interpenetrated network material advantages for absorption of crude oil and petroleum products. Crude oil uptake with up to more than 40 times of polymer weight and fast kinetics was observed in several x-D-DVB/LLDPE interpenetrated network materials. Overall, the cross-linked polyolefin interpenetrated network materials of the present disclosure exhibits a combination of benefits in oil recovery and cleanup, including (i) high oil absorption capability, (ii) fast kinetics, (iii) easy recovery from water surface, (iv) little to no water absorption, (v) minimal waste in natural resources, and (vi) cost effective and economic feasibility. All of these advantages can dramatically reduce the environmental impacts from oil spills.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A polyolefin interpenetrated network comprising a soft polyolefin network and a rigid polyolefin network, wherein the rigid polyolefin network is either amorphous with a Tg of at least 50° C. or semi-crystalline with a Tm of no less than 35° C., wherein the soft polyolefin network is represented by formula (I)

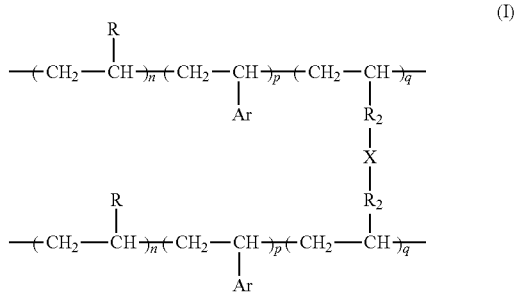

wherein ($CH_2$—CH(R)) represents the same or different olefin repeating unit; R is independently H or a $C_1$-$C_{28}$ linear, branched, or cyclic alkyl moiety; n is an integer greater than about 500; ($CH_2$—CH(Ar)) represents the same or different aromatic repeating unit; Ar is an aryl moiety that can be substituted with one or more $R_1$ groups; wherein $R_1$ is a $C_1$ to $C_{10}$ linear, branched, or cyclic alkyl moiety that can be substituted with one or more $C_1$ to $C_5$ alkyl groups; p is an integer in the range from 0 to 15,000; $R_2$ is either present or absent and when $R_2$ is present, $R_2$ is a $C_1$ to $C_{10}$ linear, branched, or cyclic alkyl moiety that can be substituted with one or more $C_1$ to $C_5$ alkyl groups; X is a cross-linking moiety resulting; and q is an integer greater than about 5.

2. The polyolefin interpenetrated network of claim 1, wherein the polyolefin interpenetrated network is in the form of either an interpenetrating polymer network (IPN) or a semi-interpenetrating polymer network (SIPN).

3. The polyolefin interpenetrated network of claim 1, wherein the rigid polyolefin network is represented by formula (II):

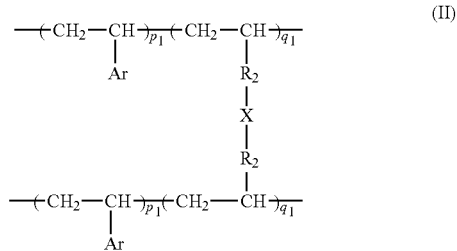

wherein ($CH_2$—CH(Ar)) represents the same or different aromatic repeating unit; Ar is an aryl moiety that can be substituted with one or more $R_1$ groups; wherein $R_1$ is a $C_1$ to $C_{10}$ linear, branched, or cyclic alkyl moiety that can be substituted with one or more $C_1$ to $C_5$ alkyl groups; p1 is an integer greater than about 500; $R_2$ is either present or absent and when $R_2$ is present, $R_2$ is a $C_1$ to $C_{10}$ linear, branched, or cyclic alkyl moiety that can be substituted with one or more $C_1$ to $C_5$ alkyl groups; X is a cross-linking moiety; and q1 is an integer greater than about 5.

4. The polyolefin interpenetrated network of claim 1, wherein the rigid polyolefin network is represented by formula III:

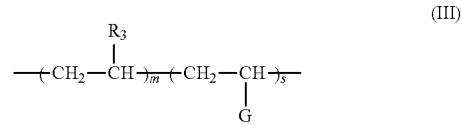

wherein ($CH_2$—CH($R_3$)) represents a $C_2$-$C_8$ alpha olefin; $R_3$ is independently H or a $C_1$-$C_6$ linear, branched, or cyclic alkyl or aromatic moiety; m is an integer greater than about 500, G is a pendant side group, which is different from $R_3$ and can be linear or branched alkyl group, or a cyclic aliphatic or aromatic group; s is an integer in the range from 0 to 5,000; and the ratio of m to s is greater than about 5.

5. The polyolefin interpenetrated network of claim 1, wherein the rigid polyolefin network is a semi-crystalline polyolefin thermoplastic that has a Tm of not less than about 35° C.

6. The polyolefin interpenetrated network of claim 1, wherein the polyolefin interpenetrated network has a weight ratio of from about 1:10 to about 10:1 of the soft polyolefin network of formula (I) to the rigid polyolefin network.

7. The polyolefin interpenetrated network of claim 6, wherein the soft polyolefin network includes from about 70 mole % to about 99.9 mole % of one or more $C_{4-12}$ aliphatic olefins as ($CH_2$—CH(R)), from about 0 to 30 mole % of one or more ($CH_2$—CH(Ar)) and from about 0.1 to 3 mole % of a cross-linker and wherein the rigid polyolefin network is a linear low density polyethylene.

8. The polyolefin interpenetrated network of claim 1, wherein the polyolefin interpenetrated network is in the form of a foam or film.

9. A process of making a polyolefin interpenetrated network, the process comprising:
mixing a precursor to the soft polyolefin network of formula (I) of claim 1 with a precursor to the rigid polyolefin network of claim 1 to make a polyolefin interpenetrated network according to claim 1.

10. A method of recovering hydrocarbon, the method comprising contacting at least one hydrocarbon with the polyolefin interpenetrated network of claim 1 to absorb the at least hydrocarbon in the polyolefin interpenetrated network.

11. The method of claim 10, wherein X is a cross-linking moiety that is a residue formed by thermal cycloaddition reaction between two pendant styrene units.

12. The method of claim 10, wherein the soft polyolefin network is completely amorphous.

13. The method of claim 10, wherein the soft polyolefin network has a Tg of less than about 10° C.

14. The method of claim 10, comprising contacting the polyolefin interpenetrated network with crude oil as the at least one hydrocarbon.

15. The method of claim 10, further comprising collecting the polyolefin interpenetrated network containing the at least one hydrocarbon and separating the at least one hydrocarbon from the polyolefin interpenetrated network.

16. The method of claim 10, further comprising heating the polyolefin interpenetrated network containing the at least one hydrocarbon to separate the at least one hydrocarbon from the polyolefin interpenetrated network.

17. The method of claim 16, further comprising decomposing the polyolefin interpenetrated network containing the at least one hydrocarbon to hydrocarbons without residue.

18. A method of recovering a hydrocarbon, the method comprising:
heating a polyolefin interpenetrated network according to claim 1 and containing at least one liquid hydrocarbon to release the at least one liquid hydrocarbon from the polyolefin interpenetrated network.

* * * * *